US010342698B2

United States Patent
Tai et al.

(10) Patent No.: US 10,342,698 B2
(45) Date of Patent: *Jul. 9, 2019

(54) IMPLANTABLE OXYGEN GENERATOR AND TRANSPORTER

(71) Applicants:California Institute of Technology, Pasadena, CA (US); University of Southern California, Los Angeles, CA (US); Doheny Eye Institute, Los Angeles, CA (US)

(72) Inventors: Yu-Chong Tai, Pasadena, CA (US); Nicholas E. Scianmarello, Pasadena, CA (US); Karthik Murali, Los Angeles, CA (US); Mark S. Humayun, Glendale, CA (US); Ramiro Magalhaes Ribeiro, South Pasadena, CA (US)

(73) Assignees: CALIFORNIA INSTITUTE OF TECHNOLOGY, Pasadena, CA (US); UNIVERSITY OF SOUTHERN CALIFORNIA, Los Angeles, CA (US); DOHENY EYE INSTITUTE, Los Angeles, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 15/685,353

(22) Filed: Aug. 24, 2017

(65) Prior Publication Data
US 2017/0348147 A1     Dec. 7, 2017

Related U.S. Application Data

(63) Continuation of application No. 15/261,435, filed on Sep. 9, 2016, now Pat. No. 9,763,825.
(Continued)

(51) Int. Cl.
*A61F 9/00*     (2006.01)
*A61M 5/142*    (2006.01)
(Continued)

(52) U.S. Cl.
CPC ....... *A61F 9/0017* (2013.01); *A61M 5/14276* (2013.01); *A61M 37/00* (2013.01);
(Continued)

(58) Field of Classification Search
CPC .................... A61F 9/0017; A61M 2005/14204
See application file for complete search history.

(56) References Cited

U.S. PATENT DOCUMENTS 7,813,807 B2    10/2010   Franklin et al.
8,255,030 B2 *   8/2012   Petisce ............... A61B 5/14532
                                                      600/345
(Continued)

FOREIGN PATENT DOCUMENTS

| CA | 2890417 | 4/2014 |
| WO | 2014055989 | 4/2014 |
| WO | 2017044839 | 3/2017 |

OTHER PUBLICATIONS

Efron et al., "Oxygen Levels Beneath the Closed Eyelid", nvest. Ophthalmol. Visual Sci., vol. 18, No. 1, Jan. 1979, pp. 93-95.
(Continued)

*Primary Examiner* — Nathan R Price
*Assistant Examiner* — John A Doubrava
(74) *Attorney, Agent, or Firm* — Kilpatrick Townsend & Stockton LLP

(57) ABSTRACT

An implantable medical device is described. The implantable medical device includes a small molecule generator, a small molecule diffusor, and a cannula that connects the two. The small molecule generator includes an electrolyte reservoir and a set of electrodes. A first portion of the electrolyte reservoir is impermeable to a predetermined class of small molecules. A second portion of the electrolyte reservoir is permeable to the small molecules. The set of electrodes is disposed inside the electrolyte reservoir and is configured to
(Continued)

facilitate electrolysis of the small molecules based on an electric power application to the set of electrodes and on presence of electrolyte inside the electrolyte reservoir. At least a portion of the small molecule diffusor is permeable to the small molecules.

20 Claims, 14 Drawing Sheets

Related U.S. Application Data

(60) Provisional application No. 62/217,202, filed on Sep. 11, 2015.

(51) Int. Cl.
    *A61M 37/00*     (2006.01)
    *A61N 1/05*     (2006.01)
    *A61N 1/378*     (2006.01)
    *A61N 1/20*     (2006.01)

(52) U.S. Cl.
    CPC ............. *A61N 1/0543* (2013.01); *A61N 1/20* (2013.01); *A61N 1/3787* (2013.01); *A61M 2005/14204* (2013.01); *A61M 2205/04* (2013.01); *A61M 2210/0612* (2013.01)

(56) References Cited

U.S. PATENT DOCUMENTS

| | | | | |
|---|---|---|---|---|
| 9,763,825 B2* | 9/2017 | Tai | ....................... | A61N 1/3787 |
| 2006/0200097 A1* | 9/2006 | Humayun | ................. | A61F 2/16 |
| | | | | 604/288.01 |
| 2006/0247664 A1* | 11/2006 | Meng | ....................... | A61B 3/16 |
| | | | | 606/151 |
| 2008/0039792 A1* | 2/2008 | Meng | .................... | A61K 9/0024 |
| | | | | 604/114 |
| 2008/0046028 A1* | 2/2008 | Franklin | .............. | A61N 1/0551 |
| | | | | 607/53 |
| 2008/0262611 A1* | 10/2008 | Li | ..................... | B29C 66/82661 |
| | | | | 623/6.63 |
| 2009/0192493 A1* | 7/2009 | Meng | .................... | A61F 9/0017 |
| | | | | 604/513 |
| 2009/0240215 A1* | 9/2009 | Humayun | ............. | A61F 9/0017 |
| | | | | 604/290 |
| 2009/0306585 A1* | 12/2009 | Pang | ................. | A61M 5/14276 |
| | | | | 604/67 |
| 2009/0306594 A1* | 12/2009 | Pang | ................... | A61F 9/00781 |
| | | | | 604/133 |
| 2010/0168646 A1* | 7/2010 | Greenbaum | ............. | A61N 1/20 |
| | | | | 604/20 |
| 2012/0041427 A1* | 2/2012 | Caffey | ............. | A61M 5/14526 |
| | | | | 604/891.1 |
| 2013/0116665 A1* | 5/2013 | Humayun | ............. | A61M 5/162 |
| | | | | 604/891.1 |
| 2014/0058506 A1* | 2/2014 | Tai | ........................ | A61N 1/0543 |
| | | | | 623/4.1 |
| 2015/0273197 A1* | 10/2015 | Humayun | ............. | A61F 9/0017 |
| | | | | 604/23 |
| 2015/0366707 A1* | 12/2015 | Tai | ........................ | A61F 9/0017 |
| | | | | 604/8 |
| 2017/0071785 A1 | 3/2017 | Tai et al. | | |

OTHER PUBLICATIONS

Kang et al., "MEMS Oxygen Transporter to Treat Retinal Ischeimia", California Institute of Technology, Pasadena, Kang et al., Jan. 2015.
Klein , "Overview of Epidemiologic Studies of Diabetic Retinopathy", Opthalmic Epidemiology, vol. 14, Jul.-Aug. 2007, pp. 179-183.
McLeod , "Krogh Cylinders in Retinal Development, Panretinal Hypoperfusion and Diabetic Retinopathy", Acta Ophthalmologica, vol. 88, 2010, pp. 817-835.
PCT/US2016/051090 , "International Search Report and Written Opinion", dated Nov. 29, 2016, 6 pages.

* cited by examiner

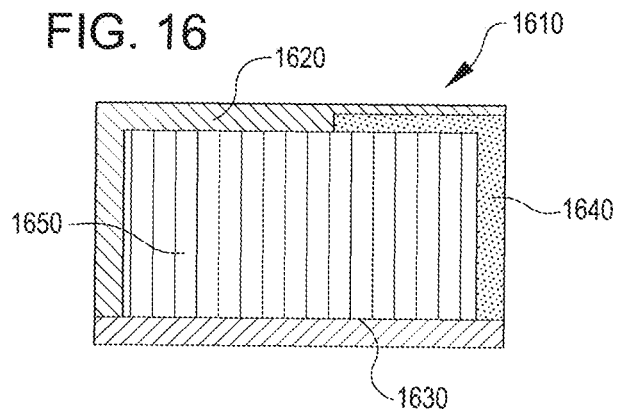
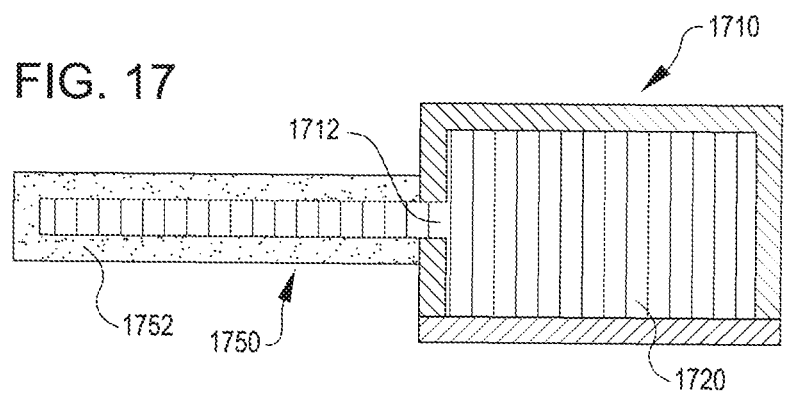
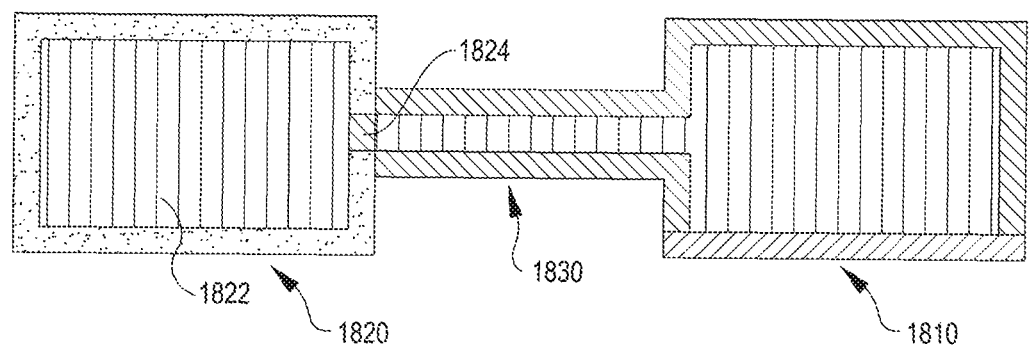

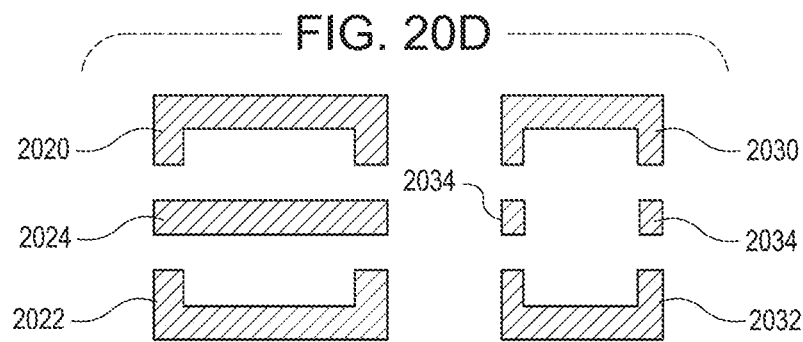
FIG. 20D
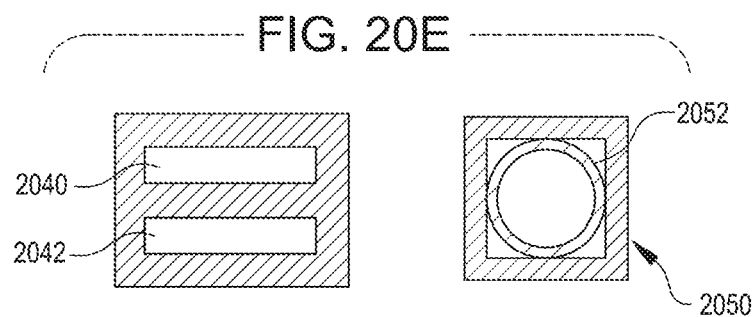
FIG. 20E
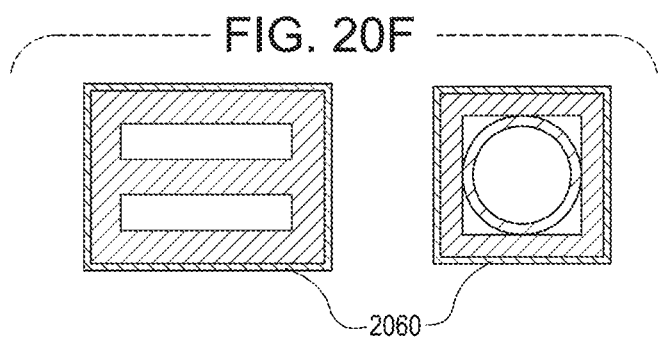
FIG. 20F
FIG. 20G
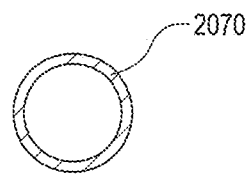
FIG. 20H
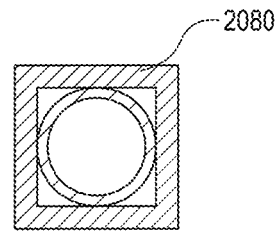

IMPLANTABLE OXYGEN GENERATOR AND TRANSPORTER

CROSS-REFERENCES TO RELATED APPLICATIONS

This application is a Continuation of U.S. patent application Ser. No. 15/261,435, filed Sep. 9, 2016, entitled "IMPLANTABLE OXYGEN GENERATOR AND TRANSPORTER", which claims the benefit of U.S. Provisional Application No. 62/217,202, filed Sep. 11, 2015, the contents of which are hereby incorporated in its entireties for all purposes.

STATEMENT AS TO RIGHTS TO INVENTIONS MADE UNDER FEDERALLY SPONSORED RESEARCH AND DEVELOPMENT

This invention was made with government support under Grant No. EY022059 awarded by the National Institutes of Health. The government has certain rights in the invention.

BACKGROUND

1. Field of the Art

Generally, embodiments of the present invention relate to methods and devices for treatment of the eyes and other areas within a body of a subject. More specifically, embodiments relate to implantable medical devices for capturing small molecule therapeutic agents or waste material and transporting them to and from structures within the body.

2. Description of the Related Art

In the United States, the leading cause of blindness is diabetic retinopathy. Diabetic retinopathy is caused by retinal ischemia, that is, inadequate blood flow to the retina caused by capillary nonperfusion. The lack of capillary blood flow starves the retina of oxygen. Retinal vein occlusion also occurs in which small veins that move blood away from the retina are blocked. A subject with retinopathy loses vision over time as retinal cells in his or her eyes die.

Other areas of the body besides the eyes can experience lack of blood flow caused by diabetes or other ailments. Restriction of blood flow to a particular portion of the body is simply called ischemia. Ischemia is often accompanied by hypoxia, which refers to the lack of oxygen ($O_2$) that blood delivers. Ischemic insults often cause severe tissue hypoxia and ultimately tissue death.

Current treatment methods for ischemic diseases are limited and do not necessarily treat the primary cause of the disease—that is, hypoxia. The mainstay of treatment for capillary nonperfusion or areas of ischemia is laser ablation. This treatment is destructive, irreversible, and can cause additional organ loss. Systemic administration of oxygen is also an option, but toting around pure oxygen or scheduling appointments for oxygen injections carries risks and is inconvenient for subjects.

Retinal ischemia can be treated with the above methods, but such treatments in the eye carry additional drawbacks. For example, laser ablation and photocoagulation can result in a constricted peripheral visual field as well as delayed dark adaptation. Other treatments have been developed for the eye, such as intravitreal injections and pars plana vitrectomies. Intravitreal injections often need to be repeated frequently and poses significant risk and cost to the patient and healthcare system. Intravitreal injections use therapeutic agents that only suppress downstream effects of the hypoxia on retinal tissue. A pars plana vitrectomy, which removes a portion of vitreous humor from the eye, may result in insufficient amounts of retinal oxygen while causing cataracts or other potential oxygen toxicity near the lens. Indeed, too much oxygen near the front (anterior) inside of the eyeball near the lens is a bad thing. It can also increase the risk of iris neovascularization as well as elevated intraocular pressure.

Therefore the current armamentarium of treatments for ischemic retinal and other diseases has a number of distinct disadvantages that need to be overcome.

BRIEF SUMMARY

Generally described is a microfabricated, implantable medical device for delivering small molecules, such as molecular oxygen ($O_2$), to areas containing tissue of interest. In an embodiment, the implantable medical device actively generates the small molecules using electrolysis within a small, semi-permeable chamber of water or other electrolyte. The small molecule generation occurs at a first location of the implantable medical device and is then transported to a second location of the implantable medical device. The two locations are remote from each other. While the first location is typically located near an external surface of a body, the second location is located in proximity of the tissue of interest. The generated oxygen is diffused from the second location to the tissue of interest.

For example, the implantable medical device includes a small molecule generator. The small molecule generator contains at least an electrolyte reservoir. The electrolyte reservoir includes an electrolyte and a set of electrodes and is defined by external membranes. At least one of the membranes is impermeable to the small molecules and at least another membrane is permeable to the small molecules. Upon an application of electric power (e.g., an application of voltage and/or current) to the set of electrodes, electrolysis occurs, thereby generating the small molecules from the electrolyte. The small molecules are diffused through the permeable membrane. The implantable medical device also includes a cannula and a small molecule diffusor. The cannula connects the small molecule generator and the small molecule diffusor, thereby providing a transport path for the small molecules from the oxygen generator to the small molecule diffusor. The small molecules are then diffused from the small molecule diffusor to the area containing the tissue of interest.

In a further example, the small molecule generator also includes a chamber. The chamber and the electrolyte reservoir share a membrane permeable to the small molecules. Other membranes of the chamber are impermeable to the small molecules. Further, an opening in the chamber is connected to the lumen of the cannula. The small molecules are generated in the electrolyte reservoir using electrolysis and diffuse into the chamber via the interfacing, permeable membrane. The cannula then transports the small molecule to the small molecule diffusor.

In the above example, at least the chamber and the electrolyte reservoir of the small molecule generator form a bag that is impermeable to the small molecules. On the other hand, the small molecule diffusor forms a permeable sac. The lumen connects the interior of the chamber to the interior of the permeable sac. The small molecules can include oxygen, where the oxygen is generated as an agent providing therapeutic benefits to the tissue of interest. For instance, the tissue may be macula of an eyeball. The chamber, the cannula, and the permeable sac can include oxygen transport substance such as at least one of perfluorocarbon, nanoporous glass, expanded polytetrafluoroethylene, or an array of suspended carbon nanotubes.

In a further example, the implantable medical device also includes an absorption bag. The absorption bag is also connected to the cannula. Thus, a small molecule transport path is also available from the absorption bag to the small molecule diffusor. The absorption bag is configured to passively absorb the small molecules from a surrounding environment. Given a concentration differential, the absorbed small molecules are transported to the small molecule diffusor for diffusion to the tissue of interest. Hence, the absorption bag acts as a passive device for supplementing the active generation of the small molecules.

In the example of the implantable hybrid medical device (e.g., containing the active small molecule generator and the passive absorption bag), the cannula can be split into multiple channels. For instance, one of the channels is connected to the small molecule generator and transports oxygen generated therefrom to the small molecule diffusor. Another channel of the cannula is connected to the absorption bag and transports oxygen absorbed thereby to the small molecule generator. A membrane that is impermeable to the small molecules may be used to split the lumen of the cannula into multiple channels.

The small molecule diffusor can similarly be split into multiple channels using the impermeable membrane. Here also, one interior channel of the small molecule diffusor is connected to the small molecule generator through a channel of the cannula. Another channel of the small molecule diffusor is connected to the absorption bag through another channel of the cannula.

In an example, the small molecules are generated via electrolysis in the electrolyte chamber. Power is supplied to the small molecule generator in order to trigger the electrolysis. Various power sources are possible. For instance, wireless power can be used where an external power source is inductively coupled to the small molecule generator. The external power source forms a primary side. In this illustration, the small molecule generator includes a coil and circuitry for the inductive coupling and to control the electric power application to the set of electrodes. The coil and circuitry form a secondary side. The circuitry also includes electrical and electronic components for controlling the electric power application and, thus, the small molecule generation, and for monitoring and reporting the amount of generated small molecules and the level of the electrolyte. A feedback look can be used to control power from the primary side. The secondary side can also include a battery that is charged through the inductive coupling. In the absence of the primary source, the battery may supply power for the electrolysis. The feedback loop may also be used for controlling the power supply from the battery.

Over time, the level of electrolyte in the electrolyte reservoir decreases. The electrolyte can be replenished. An internal hydrophilic surface of the electrolyte reservoir facilitates the replenishment via condensation. Another reservoir connected to the electrolyte reservoir can also be used, where the replenishment relies on osmosis or on valve controls. The electrolyte reservoir may additionally or alternatively include a refill port. A septum and a needle can be used to replenish the electrolyte through the refill port.

Also described are methods of manufacturing (e.g., microfabrication) of the implantable medical device. In an example, a manufacturing method includes spreading a first material on half molds, where the first material is permeable to a predefined class of small molecules upon curing. Uncured, biocompatible silicone is an example of the first material. Molecular oxygen is an example of the small molecules. The method also includes partially curing the first material on the half molds to create partially cured material halves, aligning, joining, and further curing one of the partially cured material halves with another one of the partially cured material halves to create an integrally formed silicone workpiece. The workpiece includes a chamber and a reservoir that is separated from the chamber by a membrane made of the first material. The workpiece further includes a cannula and an oxygen diffusor that is connected to the first chamber via the cannula, inserting a set of electrodes in the reservoir and a metal tube in the cannula. The method also includes depositing a second material on the chamber, reservoir, and the cannula after the placing of the set of electrodes and the metal tube. The second material is impermeable to the small molecules upon curing. An example of the second material includes parylene. Electrolyte can be inserted in the formed reservoir In addition to or in lieu of silicone and parylene, other materials may similarly be used for the permeable and impermeable membranes. For instance, expanded polytetrafluoroethylene (PTFE) and/or thin parylene (e.g., less than one µm of parylene C) can be used for the permeable membrane. Metal, glass, and/or thick parylene (e.g., more than two µm of parylene C) can be used for the impermeable membrane.

Also described are methods of use (e.g., surgical implantation) of the implantable medical device. In an example, a use method includes providing an implantable medical device, where the implantable medical device comprises a small molecule generator, a small molecule diffusor, and a cannula, where the small molecule generator is impermeable to a predetermined class of molecules and comprises an electrolyte reservoir containing electrolyte and a set of electrodes, where the small molecule diffusor is permeable to the small molecules, and where the cannula connects the small molecule generator to the small molecule diffusor, placing the small molecule diffusor inside an eyeball such as in the vitreous humor or the suproachoridal space, placing the small molecule generator between the conjunctiva and sclera of the eyeball, and attaching the small molecule generator to the sclera.

Once the implantable medical device is in place, the method also includes placing a power source at a location external to the eyeball and applying power through the power source. The location is less than two centimeters away from a coil of the small molecule generator and at an angle less than twenty degrees relative to the coil. Applying the power causes a voltage application and/or a current application to the set of electrodes based on inductive coupling through the coil, thereby generating the small molecules in the electrolyte reservoir through electrolysis. A permeable portion of the electrolyte reservoir facilitates diffusion of the small molecules into the cannula. A lumen of the cannula facilitates transportation of the small molecules to the small molecule diffusor. A permeable portion of the small molecule diffusor facilitates diffusion of the small molecules into the eyeball.

A further understanding of the nature and the advantages of the embodiments disclosed and suggested herein may be realized by reference to the remaining portions of the specification and the attached drawings.

BRIEF DESCRIPTION OF THE DRAWINGS

FIG. 16 illustrates an example configuration of an electrolyte chamber for condensation-based electrolyte refilling, in accordance with an embodiment.

FIG. 17 illustrates an example configuration of an electrolyte chamber for osmosis-based electrolyte refilling, in accordance with an embodiment.

FIG. 18 illustrates an example configuration of an electrolyte chamber for electronic control of electrolyte refilling, in accordance with an embodiment.

FIGS. 20A-20H illustrate an example of a process for manufacturing an implantable medical device that includes at least an oxygen generator, a cannula, and an oxygen diffusor, in accordance with an embodiment.

DETAILED DESCRIPTION

Figure 1:
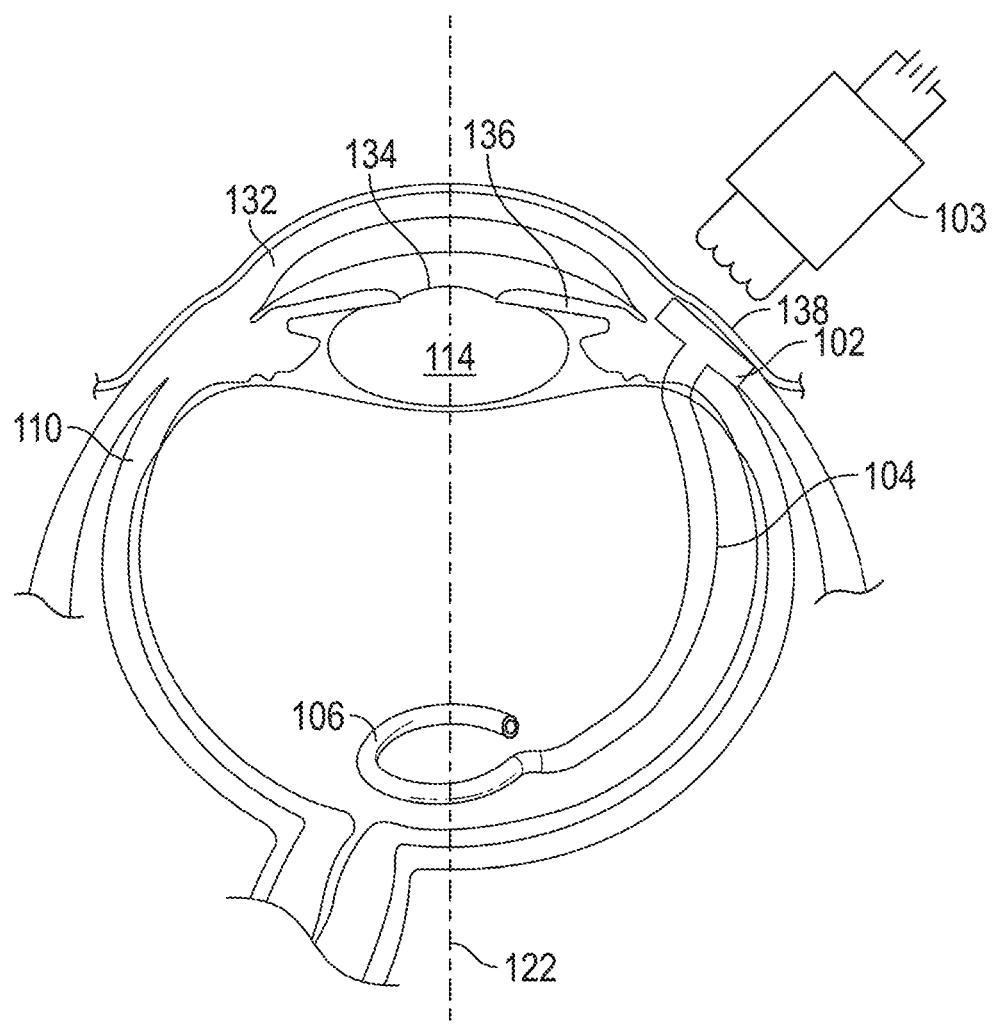
FIG. 1 illustrates an example of placing an implantable medical device such that a particular oxygen flow is achieved in proximity of a targeted tissue, in accordance with an embodiment.

Medical devices, their methods of manufacture, and methods for their implantation and use are described. The medical devices generate and capture, in the body, any biologically or chemically active agent that may have therapeutic benefits. They then deliver the agent to another part of the body.

Particularly described as an exemplary device to treat ischemic retinal diseases by supplying oxygen. The device includes an active oxygen generator and a transporter. Specifically, the device includes a reservoir, a cannula, and a diffusor, where the cannula connects the reservoir and the diffusor. The reservoir contains an electrolyte and a set of electrodes, among other components. Electrolysis occurs within the reservoir upon an electric power application (voltage and/or current) to the electrodes, thereby generating oxygen. The oxygen is transported via the cannula to the diffusor for diffusion out to surrounding tissue. The diffusor can be placed in proximity of tissue of interest, such as by the macula, and diffuses oxygen to the tissue. On the other hand, the reservoir can be placed at a location remote from the tissue. In an example, the device also includes a passive oxygenator to supplement the active oxygenation. Specifically, a passive absorption bag is connected to the cannula. This bag allows passive absorption of oxygen from an oxygen-rich zone for delivery, whereby the cannula transports the absorbed oxygen to the diffusor for diffusion to the tissue. In this example, the absorption bag and, optionally, the reservoir, are placed in the subconjunctival space. Depending on the needed level of oxygenation, the device can be utilized in the active and/or passive mode. For instance, during nocturnal sleep, the active oxygenator may be powered up to generate and deliver the needed oxygen. For remaining times of the day, the passive oxygenator provides a sufficient level of oxygen on its own. Thus, across all times of the day, proper levels of oxygen are delivered to the tissue, reducing the risk of ischemia and loss of vision, and avoiding laser photocoagulation and, possibly, a pars plana vitrectomy.

U.S. Patent Application Publication No. US 2015/0366707, titled "small molecule transport device for drug delivery or waste removal" describes a passive oxygenator and is incorporated herein by reference in its entirety. U.S. Patent Application Publication No. 2015/273197, titled "implantable oxygenator with self-contained electrolyte," describes an active oxygenator prototype, where the electrolysis occurs in a diffusor, as opposed to a remote electrolyte reservoir.

In contrast, embodiments of the present disclosure include an active oxygen generator and a transporter, where the active oxygen generator is remote from the diffusor and enables electrolysis remotely from the diffusor, and where the transporter transports the generated oxygen to the diffusor. The embodiments also describe a hybrid device that relies on both active oxygenation generation and passive oxygenation, along with oxygen transportation.

FIG. 1 illustrates an example of placing an implantable medical device such that a particular oxygen flow is achieved in proximity of a targeted tissue. In the example, the implantable medical device provides an active oxygen generator and transporter. Specifically, the implantable medical device includes an oxygen generator 102, a cannula 104, and an oxygen diffusor 106. The cannula 104 connects the oxygen generator 102 and the oxygen diffusor 106. The oxygen generator 102 actively generates oxygen. The cannula 104 transports the generated oxygen to the oxygen diffusor 106. The oxygen diffusor 106 diffuses the oxygen to the targeted tissue. Details of the components of the implantable medical device are further illustrated in the next figures.

In an example, the targeted tissue is macula of an eye. In this example, the oxygen generator 102 is placed remotely from the macula. Various placement locations are possible. For instance, the location can depend on the way the oxygen generator 102 is powered, on whether the implantable device also includes a passive oxygenator, and/or the relative arrangement of the oxygen generator 102 and the passive oxygenator. The oxygen generator 102 can be held in place through suturing or tacking to surrounding tissue.

Particularly, if wireless power is used, the oxygen generator 102 is placed near an external surface of the eye, thereby enabling wireless charging from an external power source 103 via inductive coupling. Accordingly, to the side of the lens 114, cornea 132, pupil 134, and iris 136, the oxygen generator 102 sits under conjunctiva 138. The external power source 103 can be positioned in proximity to the oxygen generator 102.

Likewise, if a passive oxygenator is collocated with the oxygen generator 102, the subconjunctival space provides an effective placement location for passively absorbing oxygen, at least during daytime. Example arrangement of the passive oxygenator are further illustrated in the next figures.

The cannula 104 pierces the sclera 110, turns to the rear, and ends up near the retina. The oxygen diffusor 106 connects with the cannula 104 such that the interior of the oxygen generator 102 is connected in a constant fluid path to the interior of the oxygen diffusor 106.

The diffusion of the oxygen through the oxygen diffusor 106 can be passive. Specifically, the oxygen is released, discharged, or delivered through a membrane of the oxygen diffusor 106. The membrane is permeable to the oxygen. The diffusion occurs given an oxygen pressure variance between the interior of the oxygen diffusor 106 and the surrounding environment.

The oxygen diffusor 106 has a hook-like shape. Other shapes are also possible and are illustrated in the next figures. An inside diameter of the oxygen diffusor 106 is positioned such that it is symmetrically placed around an optical axis 122, where the optical axis 122 is centered through the macula and the lens 114. Thus, the oxygen diffusor 106 substantially surrounds the macula without obstructing it.

In an example, once the implantable device is in place, the external power source 103 is placed within two centimeters away and within a twenty degree relative angle to the oxygen generator 102. In turn, the oxygen generator 102 generates oxygen, which is then transported to the oxygen diffusor 106. The corresponding oxygen pressure at the oxygen diffusor 106 is in excess of 200 mmHg, thereby providing adequate oxygenation to the macula.

Although FIG. 1 describes the macula as an example of targeted tissue, other targeted tissues are also possible. Generally, the implantable medical device can be implanted next to any targeted tissue, such as one at risk of ischemia or necessitating a particular oxygen flow. For instance, the implantable medical device can be used to deliver oxygen to parts of the central nervous system to alleviate hypoxia from an ischemic stroke. Likewise, the embodiments are not limited to delivery of oxygen ($O_2$). Instead, oxygen is an example of a predetermined class of small molecules. The implantable medical device can generate, transport, and/or diffuse other types of small molecules, such as carbon dioxide ($CO_2$) or nitrous oxide ($N_2O$). Generally, the predetermined class of small molecules can include a therapeutic agent for effective treatment of a targeted tissue. Ischemia can be found throughout the body in many disease processes, and with differing form factors embodiment devices can help treat it. The implantable medical device can be used to deliver or manipulate the distribution of other gases in the body. Carbon dioxide and nitrous oxide are biologically active gases that have important physiological roles. They may be redistributed in order to normalize a pathological process. Patients with chronic obstructive pulmonary disease may retain carbon dioxide in pathologic amounts. Accordingly, the implantable medical device can be used to shunt excess levels of carbon dioxide and avoid toxic buildup of this gas.

Hence, the oxygen generator 102 is an example of a small molecule generator and the oxygen diffusor 106 is an example of a small molecule diffusor. In other words, the implantable medical device more generally includes a small molecule generator and a small molecule diffusor, interconnected via a cannula 104. The small molecule generator actively generates small molecules. In an example, the small molecules are actively generated from electrolysis of an electrolyte within the small molecule generator. The electrolysis occurs upon an electric power application (e.g., voltage application and/or current application) to a set of electrodes that are located within the small molecule generator and are in contact with the electrolyte. The cannula 104 transports the generated small molecules to the small molecule diffusor. In turn, the small molecule diffusor diffuses the small molecules to the surrounding environment. The diffusion can be passive given a pressure variance, where the small molecules are released, discharged, or delivered through a membrane of the small molecule diffusor, where the membrane is permeable to the small molecules. To reduce, limit, or avoid diffusion of the small molecules from other parts of the implantable device, the small molecule generator and the cannula 104 can have a membrane that is permeable to the small molecules. These and other features of the implantable medical device are further described in connection with the next figures. In the interest of clarity of explanation, oxygen is used as an example of the small molecules.

Figure 2:
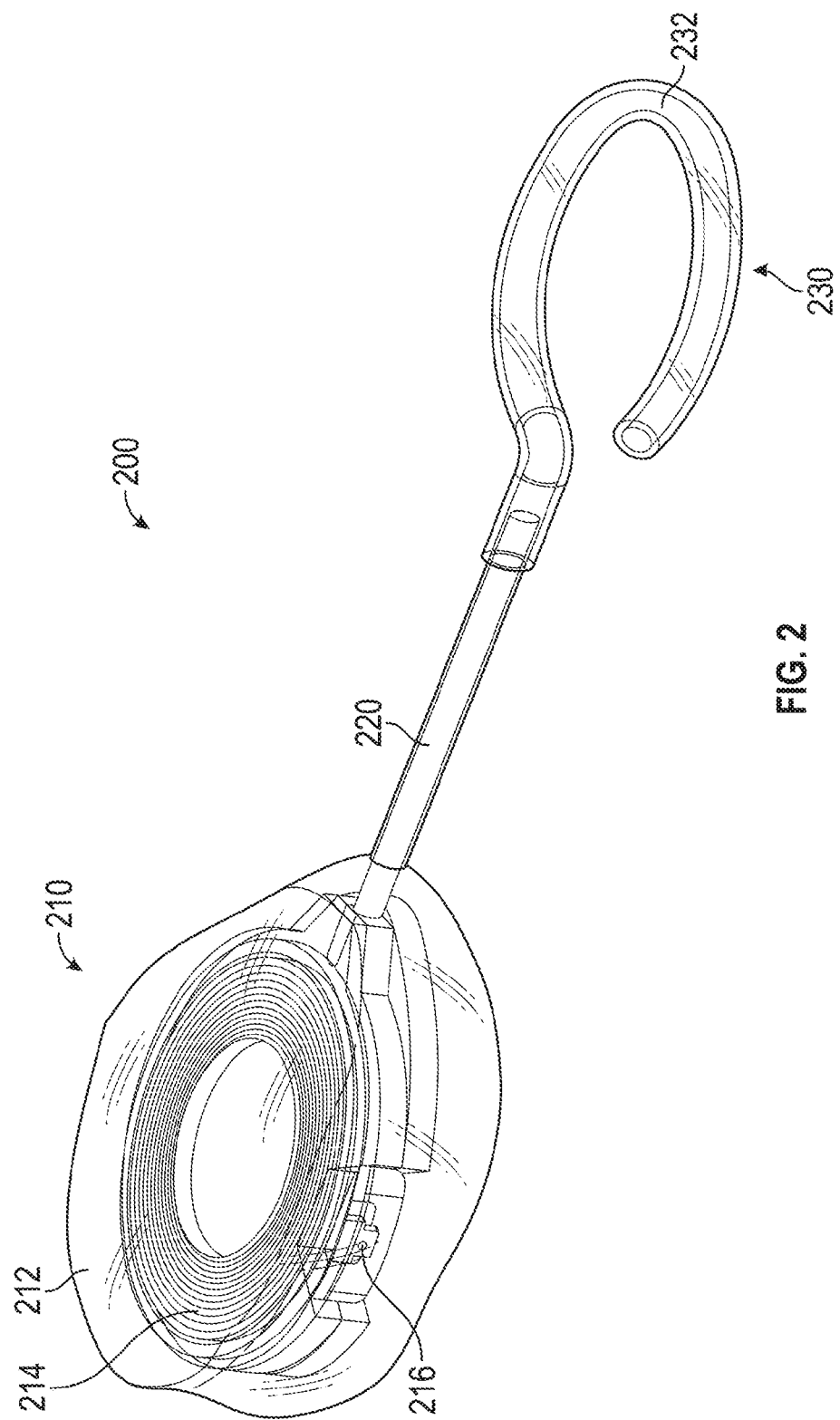
FIG. 2 illustrates an example of an implantable medical device, in accordance with an embodiment.

FIG. 2 illustrates an example of an implantable medical device 200. The implantable medical device 200 includes an oxygen generator 210 and an oxygen diffusor 230 remote from each other and interconnected via a cannula 220. More specifically, a lumen of the cannula 220 connects an interior of the oxygen generator 210 to an interior of the oxygen diffusor 230, thereby providing a constant fluid path for transporting oxygen. The cannula 220 has a structure that is narrower than the structure of the oxygen generator 210 and the structure of the small molecule diffusor 230 to allow the transportation of oxygen. Oxygen is generated in the oxygen generator 210 at a particular pressure and travels along the fluid path to the oxygen diffusor 230 given a pressure differential.

In an example, the oxygen generator 210 is formed as a bag 212 that defines the interior of the oxygen generator 210. Multiple components, such as a coil 214, circuitry 216, and other component, are places inside the interior. The components are further described in connection with the next figures. The bag 212 may be foldable, rollable, and/or stretchable and may be made out of a biocompatible silicone. To avoid diffusion of oxygen from the interior of the bag 212 to the surrounding environment, the external surface of the bag 212 is coated with a biocompatible material impermeable to oxygen, such as parylene C. The bag 212 can also include tabs, each having a through hole. A through hole is sized for sutures and can be called a suture hole. Further, handles can be attached to the bag 212. The handles can be used to place the bag 212, hold the bag 212 for suturing, and pull the cannula 220 and the oxygen diffusor 230. A view port can be integrated with the external surface of the bag 212, and can be made of a transparent material such as glass. The view port allows visual inspection of components within the bag 212 including, for instance, a level of electrolyte. Further, the bag 212 may include a refill port usable to fill and refill the bag 212 with an electrolyte.

In an example, the cannula 220 includes a biocompatible metal sheet or plate, such as a biocompatible stainless steel tube, that can be easily manipulated so as to rigidly maintain the implantable medical device's 200 shape and location. The tube is pliable so that it can be bent and keep its bend shape or re-bent to a straight shape and keep its straight shape. The bending can be performed with a surgeon's hand or by surgical instruments. The cannula 220 can be made out of biocompatible silicone and also be coated with a biocompatible material impermeable to oxygen, such as parylene C to avoid permeation of oxygen from the lumen to the external environment.

The oxygen diffusor 230 is formed as a discharge sac 232 that defines the interior of the oxygen diffusor 230. The discharge sac 232 can be foldable, rollable, and/or stretchable and may be made of different biocompatible materials permeable to oxygen, such as silicone.

Dosing and targeted release can be controlled by material properties of the implantable device. Controlling the thickness of silicone and parylene C, and/or using other materials such as expanded PTFE, metals, glasses, parylene HT, parylene D, parylene N, etc. can determine the permeation rate (dosing). The bag 212, cannula 220, and discharge sac 232 are integrally formed with the same thickness of silicone, a single adjustment to how much silicone is distributed on a mold can determine the respective permeation rates. The bag 212 and the cannula 220 are coated with an impermeable coating (e.g., parylene C) and, thus, their permeability is relatively independent of how much silicone is distributed on the molds and significantly limits the permeation rates of the oxygen through these parts of the implantable medical device 200.

"Permeability" of a material is typically in relation to a size of substance of interest. A Stokes-Einstein radius or a Stokes diameter is a measure of the diffusion properties of a substance. A "Stokes diameter" is an equivalent diameter of a hard sphere that a molecule possesses in terms of its diffusion rate. A molecule can pass through thin materials with pores that have a Stokes diameter that is about 1 to about 5 times the Stokes diameter of the molecule.

"About" includes within a tolerance of ±0.01%, ±0.1%, ±1%, ±2%, ±3%, ±4%, ±5%, ±8%, ±10%, ±15%, ±20%, ±25%, or as otherwise known in the art.

The bag 212, the cannula 220, and the discharge sac 232 can have different shapes, surface areas, and dimensions. Generally, the geometry of the bag 212 can be set to support a desired rate of oxygen generation and storage. The geometry of the cannula 220 can be set to achieve a desired rate of oxygen transport. And the geometry of the discharge sac 232 can be designed to achieve a desired permeation rate. Hence, the geometries are application dependent and can be designed for the specific task the implantable medical device 200 is to perform. Generally, the bag 212 may be larger than the discharge sac 232 such that a large amount of oxygen is generated and stored in the bag 212 to support a desired rate of oxygen permeation through the discharge sac 212.

The oxygen diffusion out of the discharge sac 232 into a deficient region of the body lowers the device's internal concentration. This in turn pulls oxygen from the bag 212 where oxygen is generated and stored at relatively higher concentration and pressure, thereby adequately supplying oxygen to the discharge sac 232 via the lumen of the cannula 220.

For example, while the bag 212 may have a cylindrical shape with about one centimeter diameter and a particular thickness (e.g., twelve mm), the discharge sac 232 may have a hook-like shape with the same diameter and half the thickness. The cannula 220 can be small in order to minimize the size of the incision during surgery. For example, the cannula 220 can be made to have a perimeter or circumference less than six mm in order to fit within a three mm or larger incision. Since the discharge sac 232 is made of thin silicone and is foldable, rollable, and/or stretchable, its flexibility would allow it to enter through a small incision.

In a simulation, about 2.4 mol/m$^3$ and about 0.05 mol/m$^3$ of oxygen flow to the inner retina is needed during the nighttime and daytime, respectively. These values are the best known estimates for 20% ischemia. In an in vitro experimentation, the implantable medical device 200 can supply about 253 mmHg (0.43 mol/m$^3$) of oxygen. At nighttime, the supply of stored oxygen in the bag 212 lasts for about 2.14 hours. During the daytime, the supply lasts for about 4.11 hours. Thus, for a full night (about eight hours), it may be sufficient to actively generate oxygen at two hour intervals, for a total of four times. During the day time (about sixteen hours), it may be sufficient to actively generate oxygen at four hour intervals, for a total of four times. At such rates, the bag 212 can hold enough electrolyte for about a hundred days of oxygen generation. At that point, the electrolyte is half-depleted and can be replenished. Other activation intervals are possible. For example, pulsed electrolysis can be used, where the oxygen generator is powered for one minute every four minutes during nighttime and daytime. Under this approach, the power supply can be consistent over time and need not depend on the time of the day, thereby simplifying the configuration of the oxygen generator (e.g., the power supply controls).

Figure 3:
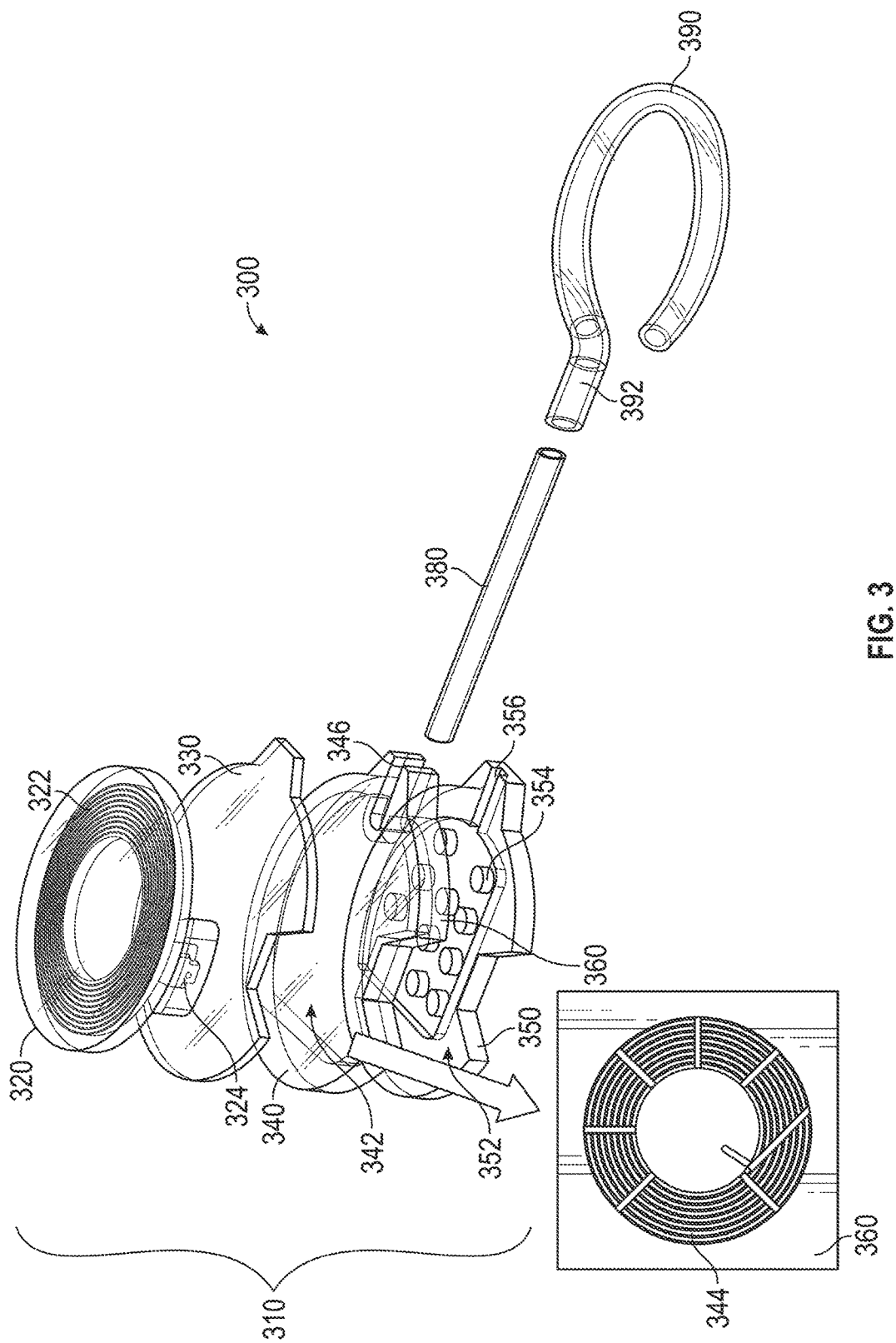
FIG. 3 illustrates an assembly of an implantable medical device, in accordance with an embodiment.

FIG. 3 illustrates an assembly of an implantable medical device 300. The implantable medical device 300 includes an oxygen generator 310, a cannula 380, and an oxygen diffusor 390. One end of the cannula 380 is connected to the oxygen generator 310. That end sits in an upper channel 346 and a lower channel 356 of the oxygen generator 310 and connects to an interior 352 of a diffusion chamber 350 of the oxygen generator 310. Another end of the cannula 380 is connected to the oxygen diffusor 390. That end fits within a channel 392 of the oxygen diffusor 390 and connects to an interior of the oxygen diffusor 390.

As illustrated, the oxygen generator 310 has a compartmentalized structure. The structure includes an insulation layer 320, a separation layer 330, an electrolyte chamber 340, and the diffusion chamber 350, all made of, for example, the same biocompatible material that is permeable to oxygen and impermeable to an electrolyte 342. Silicone is an example the biocompatible material. The separation layer 330 separates the insulation layer 320 from the electrolyte chamber 340, thereby providing an insulation of the insulation layer 320. The electrolyte chamber 340 and the diffusion chamber 350 interface through a permeable membrane 360 made of a biocompatible material permeable to oxygen, such as silicone. When assembled to form the oxygen generator 310, the different structures form a bag made of biocompatible material permeable to oxygen and impermeable to the electrolyte 342. Likewise, the cannula 380 and the oxygen diffusor 390 are made of the same biocompatible material. To limit the oxygen permeation, the exterior surfaces of the bag and the cannula 380 are coated with material impermeable to oxygen, such as parylene C. However, the exterior surface of the oxygen generator 310 is not.

In an example, the insulation layer 320 includes a coil 322 and circuitry 324, among other components, such a rechargeable power source (e.g., a lithium-ion battery). The coil 322 enables inductive coupling with an external power source, thereby facilitating wireless power transfer or charging to the circuitry 324. The coil 322 may be made of gold. The circuitry 324 includes multiple electronic and electrical components to apply electric power to a set of electrodes 344 located inside the electrolyte chamber 340 and, optionally, control the electrolysis, monitor and report the amount of generated oxygen, and monitor and report the level of the electrolyte 342.

In an example, the circuitry 324 includes a printed circuit board (PCB) on a biocompatible substrate, such as parylene C. The circuitry 324 includes a microcontroller, a memory, a radio frequency receiver, a radio frequency transmitter, a real-time clock, sensors, and other components that provide the controls based on an open loop and/or a feedback loop.

Controlling the electrolysis can include controlling the time and the rate of oxygen generation. The real-time clock, along an oxygenation schedule available from the memory can set the time (e.g., start and end) of the electrolysis. In addition or in the alternative, the start or the end can be triggered based on the rate of the oxygen generation, a level of oxygen in the electrolyte chamber 340, and/or a level of the electrolyte 342.

Controlling the rate of the rate of oxygenation can include applying particular amount of electric to the set of electrodes for a particular time period to achieve the rate. The power control can include controlling the application of voltage and/or current. The microcontroller can derive the rate based on measurements of a pressure sensor or an oxygen sensor in the electrolyte chamber 340. In addition or in the alternative, the microcontroller can derive the rate based on the level of the electrolyte 342. The level of the electrolyte 342 can be determined from measuring the amount of current needed for the electrolysis or the resistivity between the electrodes 344. The memory may store correlations between the predefined measurements, rates, and electric power application. Given the actual measurements, the microcontroller uses the correlations to set control of the electric power and, equivalently, the rate of oxygenation. The microcontroller can also store the actual measurements, rates, power applications, voltage applications, current applications, history of the electrolysis, charging times, and/or battery power level to the memory. Such data can be wireless transmitted to a remote computing device via the transmitter of the circuitry 324, thereby providing telemetry over the electrolysis. New oxygenation schedules or updates to the correlations can be wirelessly received from the remote computing device via the receiver of the circuitry 324.

In an example, the electrolyte chamber 340 defines an interior that contains the electrolyte 342. Hence, the electrolyte chamber 340 acts a reservoir that retains the electrolyte 342 and can be referred to herein as an electrolyte reservoir. The electrolyte is biocompatible and should have redox reactions at a high voltage than hydrolysis to keep efficiency high. Examples of the electrolyte includes water, magnesium sulphate, and sodium sulphate.

The electrolyte chamber 340 also includes a set of electrodes 344. The electrodes 344 are arranged such that, upon a direct current (DC) voltage application, water molecules from the electrolyte 342 are hydrolyzed. This electrolysis results in oxygen gas and hydrogen gas that can permeate out through the permeable membrane 360, into the diffusion chamber 350. Various arrangements of the electrodes are possible, including an interleaved arrangement, a spiral arrangement, or a distribution along plates. Generally, pairs of electrodes are separated by a distance to enable the application of decomposition potential, resulting in the electrolysis. The electrodes 344 may be made of a biocompatible conductive material, such as gold or platinum. A DC voltage that ranges between two to three volts may be sufficient for the electrolysis based on the type and arrangement of the electrodes 344. The electrodes 344 can be attached to the permeable membrane 360 at the lower surface of the electrolyte chamber 340, to the upper surface of the electrolyte chamber 340, or may float within the interior of the electrolyte chamber 340. The lower attachment may provide the most effective distribution of the electrolyte 342 around the electrodes 344.

In an example, the oxygen (along the hydrogen) generated in the electrolyte chamber 340 diffuses to the diffusion chamber 350 through the permeable membrane 360. When the rate of oxygenation (or, more generally, the electrolysis) is higher than the permeation rate, the electrolyte chamber 340 stores the generated gases even upon the end of the oxygenation. The stored gases diffuse into the diffusion chamber 350 at the lower permeation rate.

In an example, the diffusion chamber 350 defines the interior 352. The interior 352 has an opening connected to the lumen of the cannula 380. Hence, the oxygen (along the hydrogen) received from the electrolyte chamber 340 are passed to the lumen for transportation to the interior of the oxygen diffusor 390. The interior 352 can also include a set of posts 354 made of biocompatible silicone. The posts 354 can prevent the interior 352 from collapsing when, the pressure in the electrolyte chamber 340 is relatively higher (e.g., because of the oxygen generation).

The next figures illustrate different configurations of an implantable medical device that includes an oxygen generator, a cannula, an oxygen diffusor, and, optionally, a passive oxygenator. The orientations (top/bottom, horizontal/vertical, right/left, etc.) are described in reference to the figures. However, actual orientations depend on positioning of the implantable medical device in a body of a subject.

In the interest of clarity of explanation, the figures are simplified. Specifically, only an electrolyte chamber and, as applicable, a diffusion chamber of an oxygen generator are shown, while other layers (e.g., a circuit layer and a separation layer) are omitted. Further, only the electrolyte in the electrolyte chamber is illustrated, while electrodes and any generated gases are omitted. It is not noted that the different layers of the oxygen generator, the cannula, and the oxygen diffusor, and passive oxygenator are made of silicone, such as NuSil Technology LLC (of Carpinteria, Calif., U.S.A) MED4-4210, two-part medical grade silicone in which based and curing agent are mixed at a 10:1 ratio by weight.

The thickness of the silicone can vary across a range or can be uniform selected from the range, where the range contains 100 to 500 µm thicknesses. In an example, the thickness is set to about 240 µm. In also the interest of explanation, only the utmost exterior material is shown. The material can be coated to limit permeation. Hence, the oxygen permeable surfaces (e.g., made of the above Silicone) the electrolyte chamber, diffusion chamber, and cannula are not illustrated. Instead, an impermeable oxygen surface (e.g., made with parylene C) is illustrated.

In also the interest of clarity of explanation, some of the configurations across the figures are similar. The description of the similarities are not repeated.

Figure 4A:
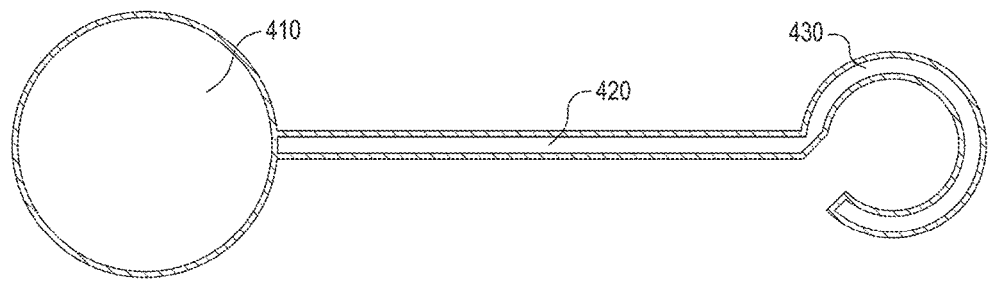
FIGS. 4A and 4B illustrate a plan view and a side view, respectively, of an implantable medical device that includes an electrolyte chamber and a diffusion chamber, in accordance with an embodiment.
Figure 4B:

FIGS. 4A and 4B illustrate a plan view and a side view, respectively, of an implantable medical device that includes an electrolyte chamber and a diffusion chamber. As illustrated in the plan view, the implantable medical device includes an oxygen generator 410, a cannula 420, and an oxygen diffusor 430. The side view illustrates a simplified configuration of the implantable device, in the interest of clarity of explanation.

Specifically, the side view shows an electrolyte chamber 412 and a diffusion chamber 413 of the of the oxygen generator 410. The electrolyte chamber 412 is coated externally with material 414 impermeable to oxygen and to an electrolyte 416, such as parylene C. The thickness of the material 414 varies within a range of two to twenty µm. In an example, the thickness is set to about five µm. The material 414 defines a first or external portion of the electrolyte chamber 412. A membrane 418 is positioned between the electrolyte chamber 412 and the diffusion chamber 413. In other words, the electrolyte chamber 412 and the diffusion chamber 413 share the membrane 418. The membrane 418 is made of material permeable to oxygen and impermeable to the electrolyte, such as NuSil Technology LLC (of Carpinteria, Calif., U.S.A) MED4-4210, two-part medical grade silicone in which based and curing agent are mixed at a 10:1 ratio by weight. The thickness of the membrane 418 varies between 100 and 500 µm. In an example, the thickness is set to about 240 µm. Because it is permeable to oxygen but not the electrolyte 416, the membrane 418 serves as an interface for diffusing oxygen from the electrolyte chamber 412 into the diffusion chamber 413. Hence, the membrane 418 defines a second or external portion of the electrolyte chamber 412, such that the membrane 418 and the material 414 form a sealed electrolyte reservoir that diffuses oxygen, but not the electrolyte 416, into the diffusion chamber 413.

The diffusion chamber 413, in addition to be defined by the membrane 418, is also coated externally with material 417. The material 417 may be impermeable to oxygen and may be the same type and have the same or substantially the same thickness as the material 414. The diffusion chamber 413 can include a substance 415 with high diffusion constant, or high oxygen solubility, such as perfluorocarbons, air, nanoporous glass, expanded polytetrafluoroethylene, or an array of suspended carbon nanotubes. This oxygen transport substance 415 allows fast transportation of the oxygen out of the diffusion chamber 413 and can inhibit condensation of water within the diffusion chamber 413. In example, the oxygen transport substance 415 stops at the opening to the lumen of the cannula 420. In another example, the oxygen transport substance 415 is placed all the way through to the end of the oxygen diffusor 430.

The cannula 420 is coated externally with material 422. The material 422 may be impermeable to oxygen and may be the same type and have the same or substantially thickness as the material 414. On the other hand, the oxygen diffusor 430 is not coated. Hence, the external membrane 432 of the oxygen diffusor 430 is a made of silicone.

As indicated above, the geometries of the oxygen generator 410 (including the two chamber 412 and 413), cannula 420, and the oxygen diffusor 430 can be set based on a targeted medical application. In the illustration of FIG. 4A, the oxygen diffusor 430 has a hook-like shape, suitable to surround the human macula without obstructing vision.

Figure 5A:
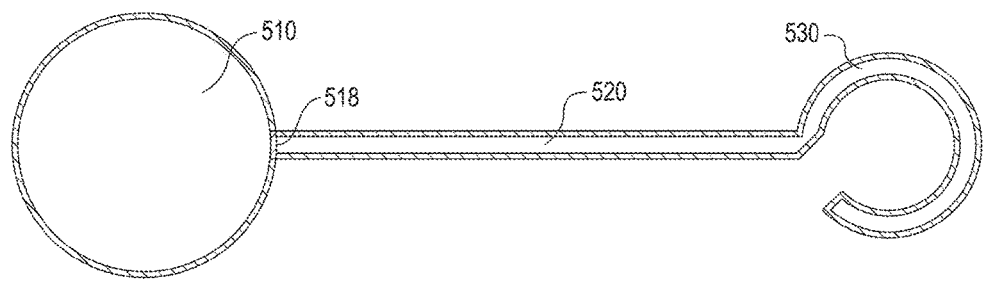
FIGS. 5A and 5B illustrate a plan view and a side view, respectively, of an implantable medical device that includes an electrolyte chamber and no diffusion chambers, in accordance with an embodiment.
Figure 5B:
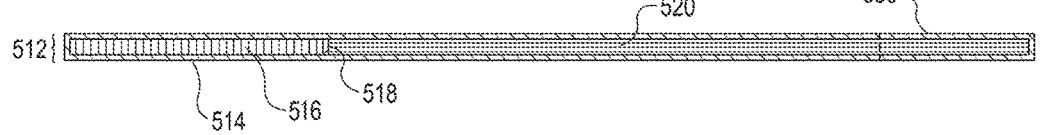

FIGS. 5A and 5B illustrate a plan view and a side view, respectively, of an implantable medical device that includes an electrolyte chamber and no diffusion chambers. This implantable medical device is similar to the one of FIG. 4, except that it does not include a diffusion chamber.

As illustrated, the implantable medical device of FIGS. 5A and 5B include an oxygen generator 510, a cannula 520, and an oxygen diffusor 530. The oxygen generator 510 includes an electrolyte chamber 512 that directly interfaces with the lumen of the cannula 520. More specifically, material 514 impermeable to oxygen and an electrolyte 516 portions of the interior of the electrolyte chamber 512. Material 518 permeable to oxygen and impermeable to the electrolyte 516 define the remaining portion(s) of the interior. The electrolyte 516 is contained within the interior. The material 518 interfaces with the lumen of the cannula 520, such that oxygen diffuses directly from the interior of the electrolyte reservoir into the lumen. Although, less complex than the two-chamber configuration of FIGS. 4A and 4B, the permeation rate of the oxygen generator 510 may be relatively lower.

Figure 6A:
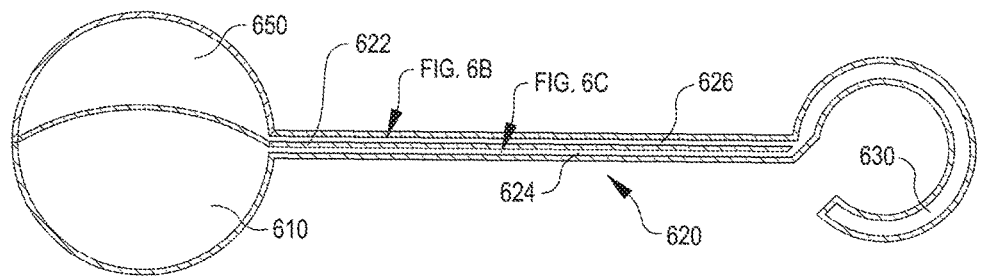
FIGS. 6A, 6B, and 6C illustrate a plan view, a right side view, and a left side view, respectively, of a hybrid implantable medical device that includes an active oxygen generator and a passive oxygenator, in accordance with an embodiment.
Figure 6B:
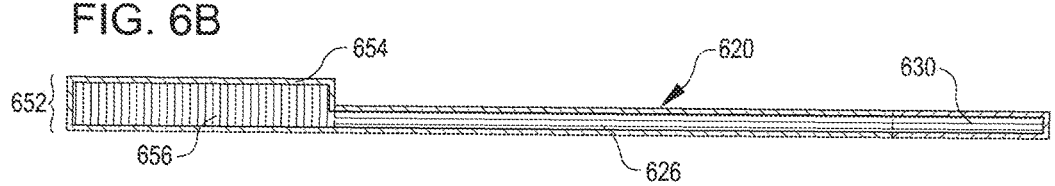
Figure 6C:
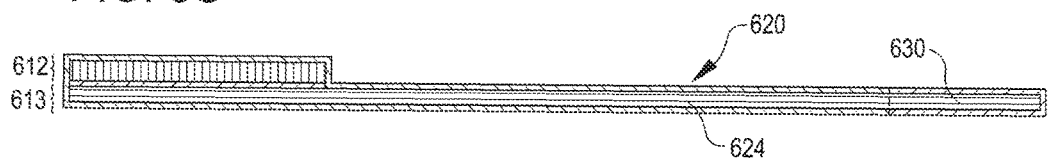

FIGS. 6A, 6B, and 6C illustrate a plan view, a right side view, and a left side view, respectively, of a hybrid implantable medical device that includes an active oxygen generator and a passive oxygenator. As illustrated in FIG. 6A, the hybrid implantable medical device includes an oxygen generator 610, a cannula 620, and an oxygen diffusor 630. These components enable an active mode of the hybrid implantable medical device. The device also includes a passive oxygenator 650, positioned adjacently to and in contact with the oxygen generator 610. The cannula 620 is split into multiple channels by a membrane 622. A first channel 624 defines a lumen to transport oxygen from the oxygen generator 610 to the oxygen diffusor 630. A second channel 626 defines a lumen to transport oxygen from the passive oxygenator 650 to the oxygen diffusor 630, where this oxygen may be, in the first place, passively received into the passive oxygenator 650. The membrane 622 can be made of material impermeable to oxygen, such as parylene C, and can have a thickness that varies between two to twenty µm. In an example, the thickness is set to about five µm.

As illustrated in FIG. 6B, the passive oxygenator 650 includes an absorption bag 652. Material 654 permeable to oxygen defines an interior of the absorption bag 652. In an example, the material 654 is made of NuSil Technology LLC (of Carpinteria, Calif., U.S.A) MED4-4210, two-part medical grade silicone in which based and curing agent are mixed at a 10:1 ratio by weight. The thickness of the material 654 varies between 100 and 500 µm. In an example, the thickness is set to about 240 µm. An opening in the interior is connected to the lumen of the second channel 626. The interior can also contain an oxygen transport substance 656.

As illustrated in FIG. 6C, the oxygen generator 610 includes an electrolyte chamber 612 and a diffusion chamber 613. This two-chamber configuration is similar to the oxygen generator 410 of FIGS. 4A and 4B.

Figure 7A:
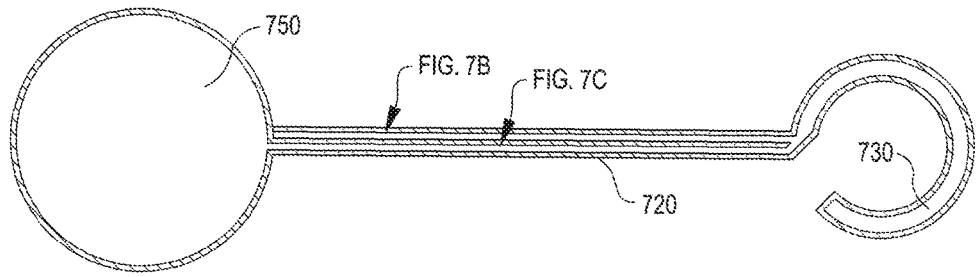
FIGS. 7A, 7B, and 7C illustrate a plan view, a right side view, and a left side view, respectively, of another example of a hybrid implantable medical device, in accordance with an embodiment.
Figure 7B:
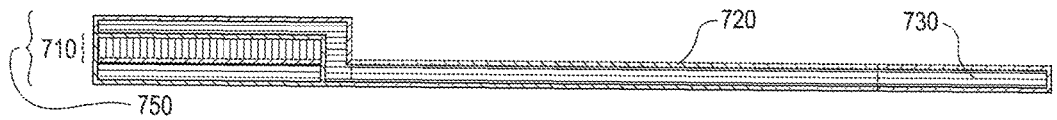
Figure 7C:
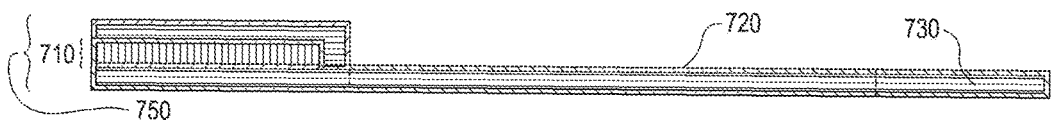

FIGS. 7A, 7B, and 7C illustrate a plan view, a right side view, and a left side view, respectively, of another example of a hybrid implantable medical device. In this example, the hybrid device includes an active oxygen generator 710 and a passive oxygenator 750, in addition to a cannula 720, and an oxygen diffusor 730. The passive oxygenator 750 is stacked on top of the oxygen generator 710. FIG. 7B illustrates the oxygen path from the passive oxygenator 750 to a corresponding channel in the cannula 720. FIG. 7C shows the oxygen path from the active oxygen generator 710 to another channel of the cannula 720.

Figure 8A:
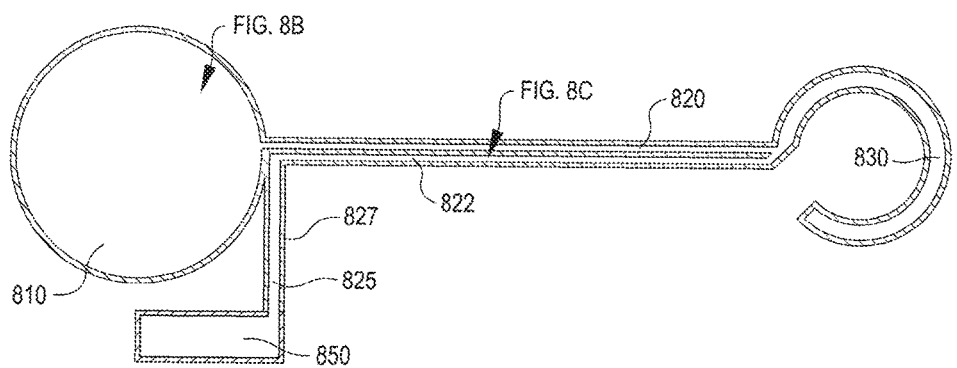
FIGS. 8A, 8B, and 8C illustrate a plan view, a right side view, and a left side view, respectively, of yet another example of a hybrid implantable medical device, in accordance with an embodiment.
Figure 8B:
Figure 8C:
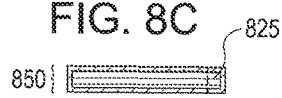

FIGS. 8A, 8B, and 8C illustrate a plan view, a right side view, and a left side view, respectively, of another example of a hybrid implantable medical device. In this example, the hybrid device includes an active oxygen generator 810 and a passive oxygenator 850, in addition to a cannula 820, and an oxygen diffusor 830. The passive oxygenator 850 is separate and remote from the active oxygen generator 810. Accordingly, the two components of the hybrid device can be placed at different locations within the body of a subject. For example, the passive oxygenator 850 can be positioned in high oxygen tension area, whereas the active oxygen generator 810 can be positioned in a different area.

As illustrated in FIG. 8A, an opening of the passive generator 850 is connected to one of the channels (shown as channel 822) of the cannula 820 via another cannula 825. In an example, the other cannula 825 is an extension of the channel 822 or is formed separately from and interfaces with the channel 822. Regardless, the cannula 825 is coated with material 827 impermeable to oxygen, such as parylene C. The thickness of the material 827 varies between two and twenty μm. In an example, the thickness is about five μm.

Figure 9A:
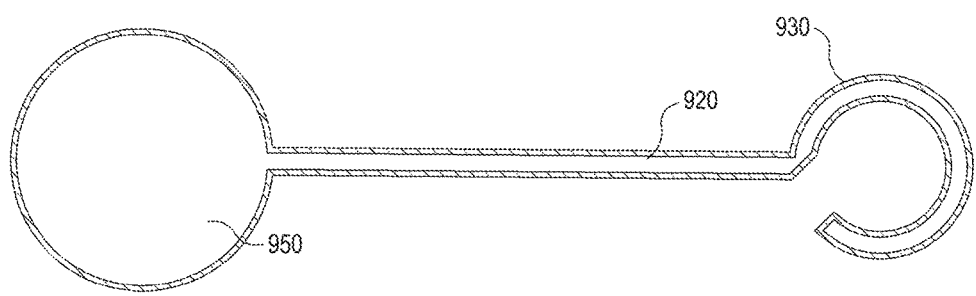
FIGS. 9A and 9B illustrate a plan view and a side view, respectively, of yet another example of a hybrid implantable medical device, in accordance with an embodiment.
Figure 9B:
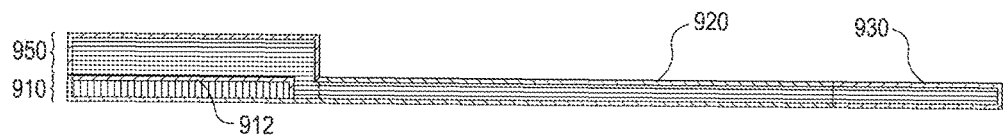

FIGS. 9A and 9B illustrate a plan view and a side view, respectively, of yet another example of a hybrid implantable medical device. In this example, the hybrid device includes an active oxygen generator 910 and a passive oxygenator 950 that are collocated, in addition to a cannula 920, and an oxygen diffusor 930. The passive oxygenator 950 is stacked on top of the active oxygen generator 910. However, the active oxygen generator 910 contains an electrolyte chamber and excludes any diffusion chamber, in a similar one-chamber configuration of FIGS. 5A and 5B. The membrane 912 that serves as an interface between the active oxygen generator 910 and the passive oxygenator 950 is made of material permeable to oxygen and impermeable to an electrolyte. For example, the membrane 912 is made of NuSil Technology LLC (of Carpinteria, Calif., U.S.A) MED4-4210, two-part medical grade silicone in which based and curing agent are mixed at a 10:1 ratio by weight. The thickness of the membrane 912 varies between 100 and 500 μm. In an example, the thickness is set to about 240 μm. The interior of the passive oxygenator 950 completely contains the active oxygen generator 910. An opening in the interior is connected to a lumen of the cannula 920. Unlike, the cannulas 720 and 820 of the above hybrid devices, the cannula 920 need not be split into multiple channels. The oxygen generated from the active oxygen generator 910 diffuses into the interior of the passive oxygenator 950 and is then transported to the lumen. However, because the exterior surfaces of the passive oxygenator 950 are permeable to oxygen, the generated oxygen may also be diffused or leaked into the surrounding environment through these exterior surfaces. Thus, this example hybrid device may be less efficient than the above hybrid devices.

Figure 10A:
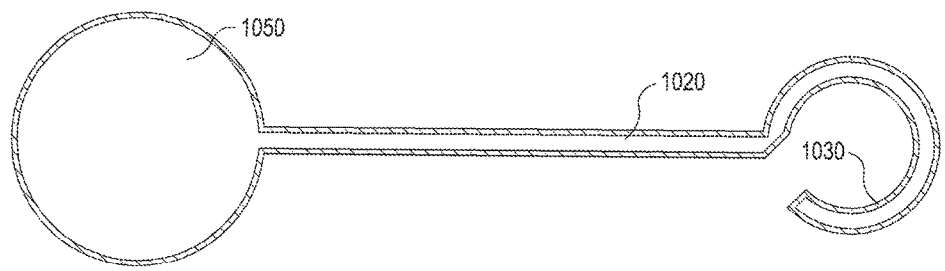
FIGS. 10A and 10B illustrate a plan view and a side view, respectively, of yet another example of a hybrid implantable medical device, in accordance with an embodiment.
Figure 10B:
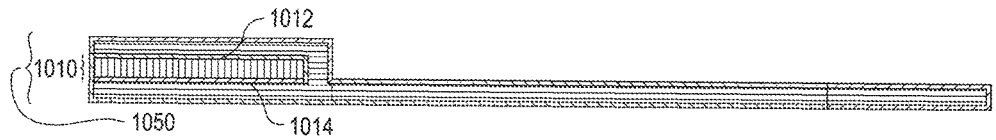

FIGS. 10A and 10B illustrate a plan view and a side view, respectively, of yet another example of a hybrid implantable medical device. In this example, the hybrid device includes an active oxygen generator 1010 and a passive oxygenator 1050 that are collocated, in addition to a cannula 1020, and an oxygen diffusor 1030. The passive oxygenator 1050 partially or fully contains the active oxygen generator 1010. In this example, a top surface of the active oxygen generator 1010 may be made of material 1012 impermeable to oxygen. In comparison, a bottom surface of the active oxygen generator 1010 may be made of material 1014 permeable to oxygen. Thus, any diffusion of generate oxygen may occur in a downward direction. However, other configurations of the surfaces of the active oxygen generator may also be possible. For example, both top and bottom surfaces may be made material impermeable to oxygen, while the right wall may be made of the permeable material, thereby reducing leakage during oxygen generation by electrolysis as the right wall provides a relatively smaller permeation area.

The configuration of an oxygen diffusor can be set to achieve a desired oxygen permeation rate from the interior of the oxygen diffusor to the surrounding environment. The oxygen permeation rate generally depends on type and thickness of material and geometry and dimensions of the oxygen diffusor.

In hybrid devices, the configuration of the oxygen diffusor can also impact oxygen flow into an opening of the interior of the diffusor and leakage around the opening, thereby impacting the permeation rate. The next figures illustrate examples of different configurations.

Figure 11:
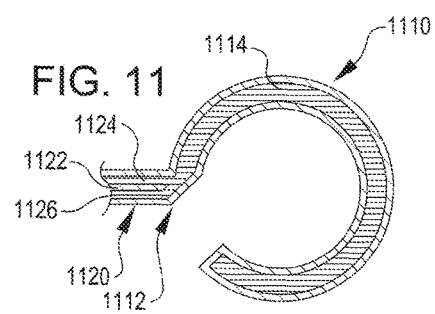
FIG. 11 illustrates an example of an oxygen diffusor suitable for a hybrid implantable medical device, in accordance with an embodiment.

FIG. 11 illustrates an example oxygen diffusor 1110 suitable for a hybrid implantable medical device. The oxygen diffusor 1110 has substantially a hook-like shape. An opening 1112 of the oxygen diffusor 1110 connects to a lumen of a cannula 1120, where the lumen is split by an oxygen impermeable membrane 1122 in two channels, illustrated as first channel 1124 and second channel 1126. The oxygen impermeable membrane 1122 ends at the opening 1112 and does not extend to an interior 1114 of the oxygen diffusor 1110. The first channel 1124 connects the interior 1114 of the oxygen diffusor 1110 to an oxygen generator, creating a first oxygen path. Similarly, the second channel 1126 connects the interior 1114 of the oxygen diffusor 1110 to a passive oxygenator, creating a second oxygen path The use of two channels is illustrative. A larger number of channels is also possible, each of which may be connected to one or a combination of oxygen generator and passive oxygenator.

Figure 12:
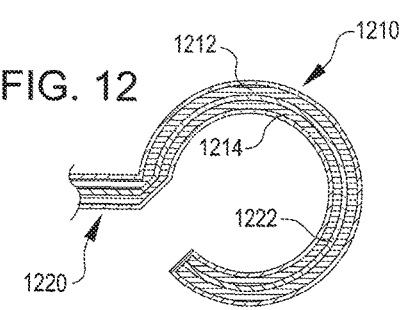
FIG. 12 illustrates another example of an oxygen diffusor suitable for a hybrid implantable medical device, in accordance with an embodiment.

FIG. 12 illustrates another example of an oxygen diffusor 1210 suitable for a hybrid implantable medical device. Here, a cannula 1220 is also split into two channels (or a larger number) by an oxygen impermeable material 1222. However, rather than stopping at the opening of the oxygen diffusor 1210, the oxygen impermeable material 1222 is extended throughout the interior, thereby creating two channels 1212 and 1214 inside the oxygen diffusor 1210. In this way, oxygen leakage can be reduced. In particular, oxygen generated from an oxygen generator and transported by the cannula 1220 into one of the channels of the oxygen diffusor 1210 (e.g., the first channel 1212) does not leak into the other channel (e.g., the second channel 1214), and back to a passive oxygenator also connected to the cannula 1220.

Figure 13A:
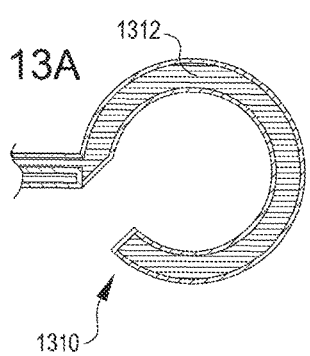
FIGS. 13A, 13B, and 13C illustrate yet another example of an oxygen diffusor suitable for a hybrid implantable medical device, in accordance with an embodiment.
Figure 13B:
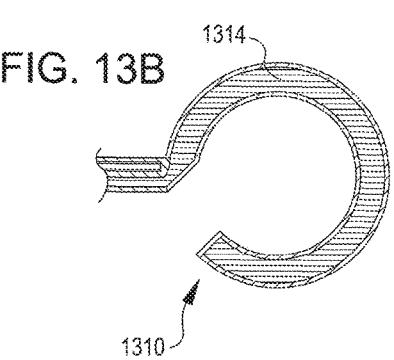
Figure 13C:
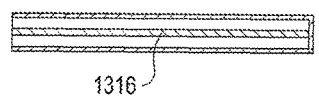

FIGS. 13A, 13B, and 13C illustrate yet another example of an oxygen diffusor 1310 suitable for a hybrid implantable medical device. Here, the oxygen diffusor 1310 is similar to the oxygen diffusor 1210 of FIG. 12 in the sense that its interior is split into two channels 1312 and 1314 (or a larger number) to minimize oxygen leakage. However, the split is vertical, rather than horizontal. In particular, an oxygen impermeable membrane 1316 is disposed vertically in the interior of the oxygen diffusor 1310 to create the two channels 1312 and 1314.

Other configurations are possible for limiting the oxygen leakage from the oxygen generator to the passive oxygenator through the oxygen diffusor. One example of such configurations includes the use of a flap valve. In particular, the flap valve may be attached to an end of the split membrane of the cannula at the opening of the oxygen diffusor. At the end, the flap valve may pivot, depending on the oxygen flow, to close or open a first channel of the cannula. The first channel corresponds to the oxygen path from the passive oxygenator. The flap valve may be made of material impermeable to oxygen, such as parylene C. Thus, the flow of oxygen generated from the oxygen generator exercises pressure on the flap valve, thereby closing the first channel and reducing the oxygen leakage to the passive oxygenator.

Other geometries of the oxygen diffusor are also possible. While the previous figures describe a hook-like shape, ring, "U," cylindrical, and/or other shapes can be used depending on the desired application. The next figures illustrate a "U" shape.

Figure 14A:
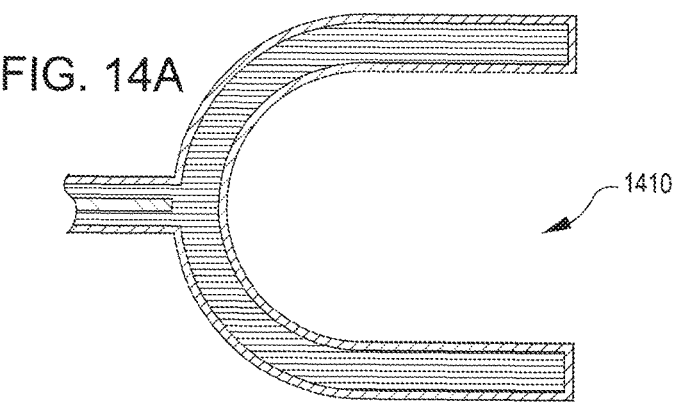
FIGS. 14A and 14B illustrate an example of an oxygen diffusor suitable for a hybrid implantable medical device, in accordance with an embodiment.
Figure 14B:
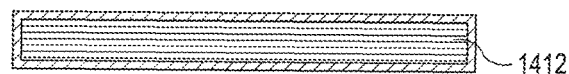

FIGS. 14A and 14B illustrate an example of an oxygen diffusor 1410 suitable for a hybrid implantable medical device. The oxygen diffusor 1410 has substantially a "U" shape. Its interior 1412 is not split into multiple channels. Similarly, to the oxygen diffusor 1110, oxygen is transported from the cannula into the single-channel interior 1412 regardless of the source of the oxygen.

Figure 15A:
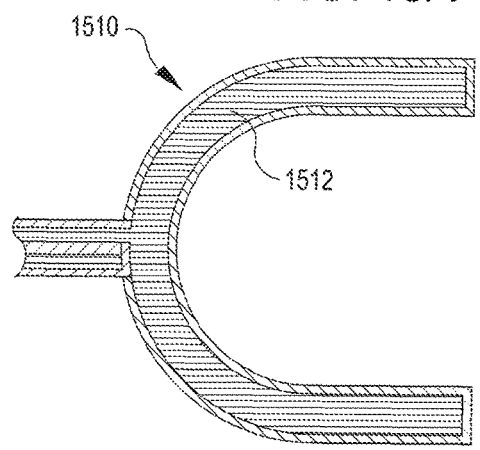
FIGS. 15A, 15B, and 15C illustrate another example of an oxygen diffusor suitable for a hybrid implantable medical device, in accordance with an embodiment.
Figure 15B:
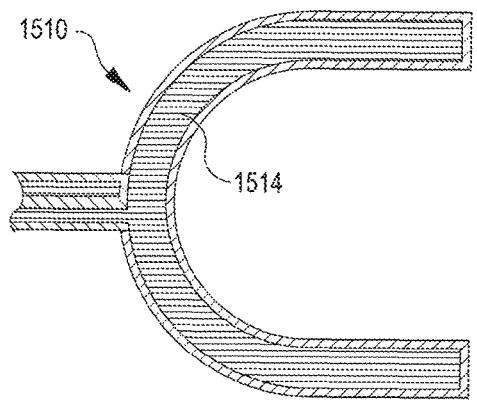
Figure 15C:

FIGS. 15A, 15B, and 15C illustrate another example of an oxygen diffusor 1510 suitable for a hybrid implantable medical device. Here, the interior of the oxygen diffusor 1510 is split into multiple channels such as a first channel 1512 and a second channel 1514. Each channel receives oxygen from a different oxygen source. Material 1516 impermeable to the oxygen splits the interior, similarly to the splitting of the oxygen diffusor 1310.

It can be expected that an implantable medical device remains implanted in a body for months, years, if not decades. As such, electrolyte within an electrolyte chamber could be depleted and may need to be replenished. Generally, once the level of electrolyte drops to a certain level (e.g., by half), refilling the electrolyte chamber should be performed. Hence, the electrolyte chamber represents an electrolyte reservoir that may be refilled over time.

Different refilling techniques are possible. One example technique may rely on a refill port of the electrolyte chamber. A surgical tool, like a syringe, a septum, and/or a needle, may be used to add electrolyte through the refill port. Other non-invasive techniques are also possible. These techniques can rely on condensation, osmosis, or electronic control and are further described in the connection with the next figures.

FIG. 16 illustrates an example configuration of an electrolyte chamber 1610 for condensation-based electrolyte refilling. As illustrated, different materials are used to define different portions of the electrolyte chamber 1610. More specifically, material 1620 may define a first portion and may be impermeable to oxygen and an electrolyte 1650. Parylene C is suitable for the material 1620. Material 1630 may define a second portion and may be permeable to oxygen and impermeable to the electrolyte 1650. Silicone is suitable for the material 1630. Material 1640 may define a third portion, may be impermeable to oxygen and the electrolyte 1650, and may facilitate condensation. For example, the material 1640 may be hydrophilic material, such as a metal or glass, or may have a hydrophilic surface (e.g. may be made with parylene C coated with a hydrophilic material). The three materials 1620, 1630, and 1640 may form a sealed reservoir for containing the electrolyte 1650. By cooling the material 1640, a vapor pressure differential is created, thereby triggering a condensation to occur the hydrophilic surface within the electrolyte chamber 1610. The cooling can be effected by blowing cold air or rinsing with cold water (e.g., at a temperature cooler than the body's temperature). For instance, when the oxygen generator is placed in the subconjunctival space, the cooling can be performed with a non-invasive tool.

FIG. 17 illustrates an example configuration of an electrolyte chamber 1710 for osmosis-based electrolyte refilling. As illustrated, the interior of the electrolyte chamber 1710 is connected to a lumen of a cannula 1750 via an opening 1712 of the interior. Electrolyte 1720 is present in both the interior and the lumen. The cannula 1750 has a membrane 1752 impermeable to the electrolyte 1720 but allowing osmosis of additional electrolyte from the surrounding environment into the lumen and, thus, the interior of the electrolyte chamber 1710. As electrolysis is performed, the ionic concentration of the electrolyte 1720 drops, thereby triggering the osmosis, which then results in the refilling of the interior of the electrolyte chamber 1710 with additional electrolyte.

FIG. 18 illustrates an example configuration of an electrolyte chamber 1810 for electronic control of electrolyte refilling. Here, the electrolyte chamber 1810 is connected to a electrolyte source 1820 via a cannula 1830. The electrolyte source 1820 can have any of the above configurations of an electrolyte chamber and, thus, can also be replenished with electrolyte via a refill port, condensation, osmosis, or other electronic-based control mechanisms. The electrolyte source 1820 stores additional electrolyte 1822 that can be supplied to the interior of the electrolyte chamber 1810. The supply path includes the lumen of the cannula 1830 and a one-way flap valve 1824. The one-way flap valve 1824 can be attached to either ends of the cannula 1830. Upon oxygen pressure exceeding a certain level, the one-way flap valve 1824 may be open to supply the additional electrolyte 1822. In an example, the oxygen pressure is increased by performing electrolysis within the interior of the electrolyte source 1820. The electrolysis can be controlled or triggered from a microcontroller of the implantable medical device.

In an example, the implantable medical device is powered wirelessly. Different electrical components may be used to this effect. They include an external components that wirelessly supply power, receive data, and/or transmit control information. The external components can include a power source, such as a battery, a power amplifier, an external induction coil, among other components. The external components can be packaged in an external device that may be worn by a subject (e.g., may be integrate in an eye cover, glasses, and the like for use with eye-based implantation of the medical device). Generally, the external components or, equivalently, the external device, form a primary side.

The implantable medical device and, more specifically, the oxygen generator can be viewed as a load that includes circuitry and an internal induction coil that wirelessly receives power and a power recovery circuit to convert received energy into DC for running the circuitry. The oxygen generator forms a secondary side. A feedback look, as described in connection with FIG. 3, can be used to control power from the primary side. The secondary side (e.g., the oxygen generator) can also include a battery that is charged through the inductive coupling. In the absence of the primary source, the battery can supply power for the electrolysis. The feedback loop may be used for controlling the power supply from the battery.

Figure 19:
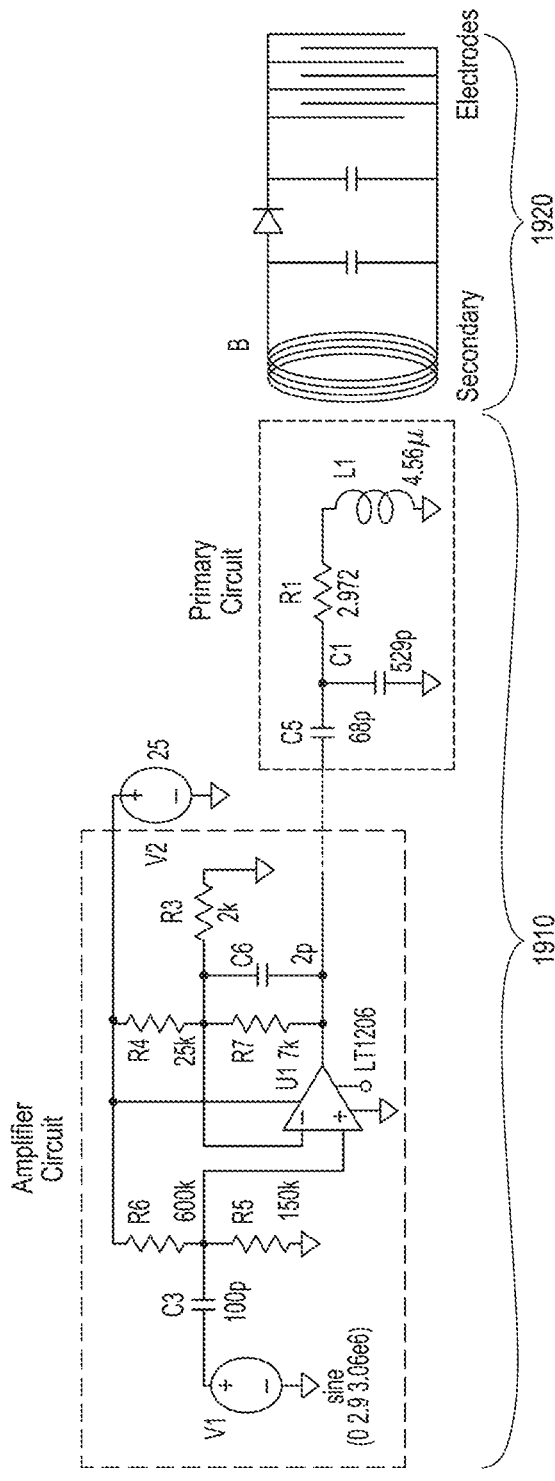
FIG. 19 illustrates example electrical components of an external device and an oxygen generator, in accordance with an embodiment.

FIG. 19 illustrates example electrical components of the external device 1910 and the oxygen generator 1920. Symbols and values of the electrical components are identified in the figure for a three MHZ operating frequencies. Other values and/or circuit configuration can be used for other operating frequencies. At the three MHz operating frequency, sufficient voltage (e.g., in the range of two to three volts) is provided for electrolysis at a distance between the coils of about two centimeters and a relative angle of up to twenty degrees.

FIGS. 20A-20H illustrate an example of a process for manufacturing an implantable medical device that includes at least an oxygen generator, a cannula, and an oxygen diffusor. Different configurations of half molds are possible, where the configurations vary the geometries of the cavities to manufacture a particular configuration of the implantable medical device. Silicone and thick parylene C (e.g., about five μm in thickness) are illustrated as two materials forming permeable membranes and impermeable membranes, respectively. Other materials can similarly be used for the membranes. For instance, expanded polytetrafluoroethylene (PTFE) and/or thin parylene (e.g., less than one μm of parylene C or other types of parylene) can be used for the permeable membrane. Metal, glass, and/or thick parylene (e.g., more than two μm of parylene C or other types of parylene) can be used for the impermeable membrane. Such materials may be added or deposited through the manufacturing process.

Figure 20A:
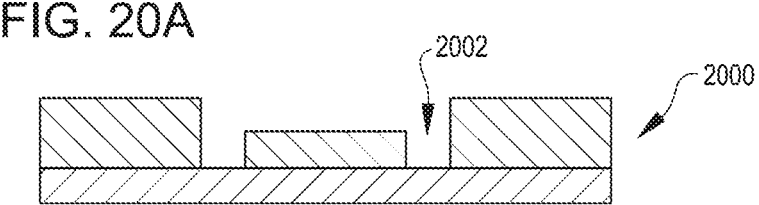

In FIG. 20A, a half mold 2000 is obtained. The half mold 2000 is created by using photoresist, masks, and exposure to visible or ultraviolet (UV) light or other electromagnetic radiation. Because masks can be easily altered, half molds can be easily customized to create custom implantable medical devices. The half mold 2000 has a cavity 2002 suitable for creating a portion of the implantable medical device. Generally, because the implantable medical device has at least three main parts (e.g., the oxygen generator, cannula, and oxygen diffusor), the half mold 2000 has at least three corresponding sections, each including a cavity 2002 dimensioned for the corresponding part of the implantable medical device.

Figure 20B:
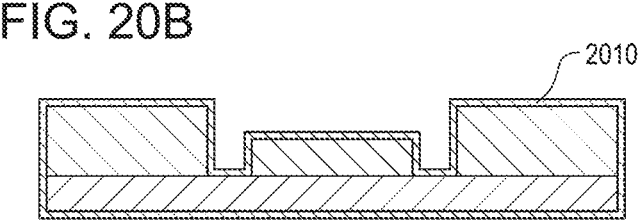

In FIG. 20B, the top part of the half mold 2020 is coated entirely with coating 2010 of parylene C in order to reduce adhesion between silicone and the half mold and, thus, increase the mold's releasability. The coating may not be necessary, depending on the surface finish of the half mold. For example, parylene C may not be needed with metal molds.

Figure 20C:
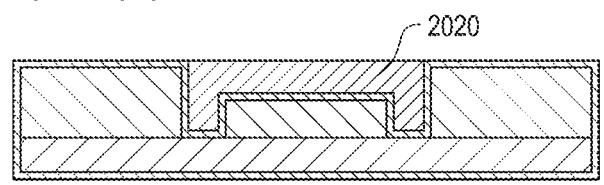

In FIG. 20C, uncured silicone 2020 is poured in the coated cavity 2002 so as to further coat the bottom and sides of the cavity 2002. It is then cured at 100° C. for five minutes.

In FIG. 20D, the cured silicone 2020 is released from the half mold 2000. Similarly, other pieces of cured silicone are released from the different half molds. Cured silicone 2022 is a mirror of the current silicone 2020 and can be used to form the oxygen generator. Similarly, cured pieces 2030 and 2032 are mirrors of each and can be used to form the cannula. Similar cured silicone pieces also exist for the oxygen diffusor. The joining edges of the pairs of cured silicone pieces are coated with uncured silicone. In an example, the two cured silicone pieces 2020 and 2022 form the electrolyte chamber and diffusion chambers of the oxygen generator when joined. Because these two chambers interface through a silicone membrane, a cured silicone strip 2024 is added in between and can extend across to form the interfacing membrane. On the other hand, no interfacing membranes exist for the cannula. Thus, cured silicone strips 2034 are added in between the joining edges of the silicone pieces 2030 and 2032 without extending across. The cured silicone strips 2024 and 2034 are manufactured in half molds as described herein above. Once the pieces are adjoined, they are then cured at 100° C. for three hours. Other main components of the oxygen generator are similarly adjoined (e.g., a separation layer, and a circuit layer).

In FIG. 20E, electrodes (not shown) are inserted in the electrolyte chamber 2040. A steel tube 2052 is also inserted in the cannula 2050.

In FIG. 20F, the oxygen generator formed by the electrolyte chamber 2040 and the diffusion chamber 2042 (and other main components) and the cannula are coated part with coating 2060 of parylene C. The thickness of the coating is about five μm. parylene C can be deposited using a chemical vapor deposition (CVD).

In FIG. 20G, the parylene C and the silicone is removed from one end 2070 of the cannula 2050. That end 2070 should connect to the oxygen diffusor.

In FIG. 20H, the parylene C and silicone free end 2070 of the cannula 2050 is inserted in an opening of the oxygen diffusor 2080 and glued. The implantable medical device can be further cured in the oven to strengthen the attachment of the cannula 2050 and the oxygen diffusor 2080.

Figure 21:
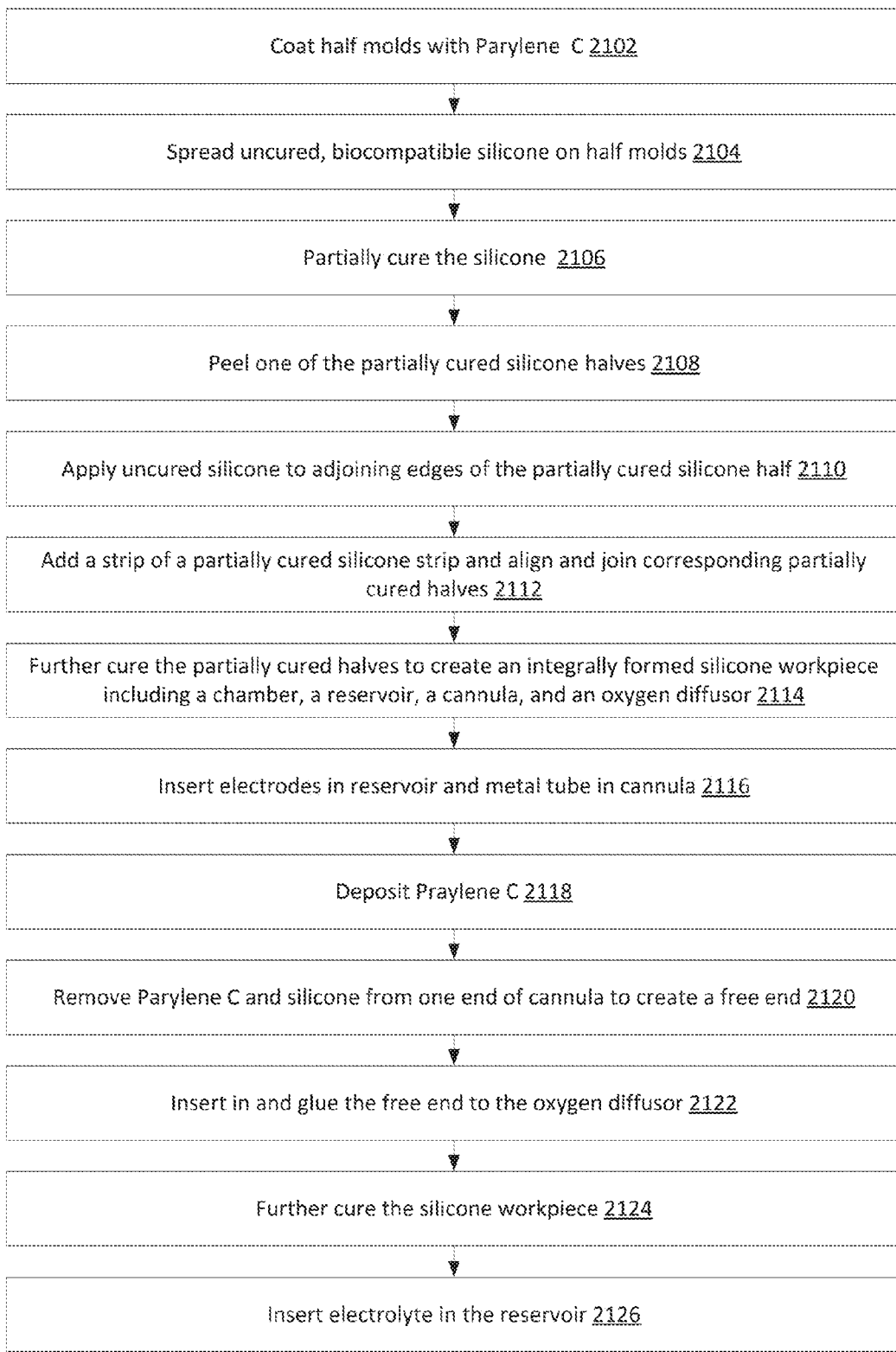
FIG. 21 is a flowchart illustrating a process for manufacturing an implantable medical device, in accordance with an embodiment.

FIG. 21 is a flowchart illustrating a process 2100 for manufacturing an implantable medical device. The implantable medical device includes at least an oxygen generator, cannula, and oxygen generator. It can also include a passive oxygenator, which can be manufactured by using suitable half molds and added to the implantable medical device during the curing process. In the interest of clarity of explanation, the oxygen generator is illustrated as a having a chamber (e.g., a diffusion chamber) and a reservoir (e.g., an electrolyte reservoir). However, the oxygen generator can include other parts, such as a circuit layer and a separation layer. These other layers can be manufactured by using suitable half molds and also added to the implantable medical device during the curing process. In also the interest of clarity of explanation, silicone and parylene C are illustrated as forming permeable membranes and impermeable membranes, respectively, of the implantable medical device. Other materials can be additionally or alternatively used. Generally, a first material permeable to a predefined class of small molecules, such as molecular oxygen (O2), can be used to form the permeable membranes. A second material impermeable to the predefined class of small molecules can be used to form the impermeable membrane. Examples of the first material include expanded polytetrafluoroethylene (PTFE), silicone, and thin parylene (e.g., less than one μm of parylene C or other types of parylene). Examples of the second material include metal, glass, and/or thick parylene (e.g., more than two μm of parylene C or other types of parylene).

In operation 2102, parylene C is coated on half molds to increase the releasability of such molds. Each half mold may have one or more cavities. Each cavity corresponds to a portion of a part of the implantable medical device (e.g., half of the chamber, half the reservoir, half the cannula, half the oxygen diffusor, etc.).

In operation 2104, uncured, biocompatible silicone is spread on the half molds. Suitable silicone includes NuSil Technology LLC (of Carpinteria, Calif., U.S.A) MED4-4210, two-part medical grade silicone in which based and curing agent are mixed at a 10:1 ratio by weight.

In operation 2106, the silicone halves are partially cured. For example, the silicone is cured at 100° C. for five minutes.

In operation 2108, a partially cured silicone half is peeled from the mold. This half has adjoining edges.

In operation 2110, uncured silicone is applied to the adjoining edges. The uncured silicone is biocompatible and is used to adjoin the silicone half to a corresponding silicone half. The operations 2108 and 2110 are repeated for different partially cured silicones halves, where each of these halves define a portion of a part of the implantable medical device (e.g., half of the chamber, half the reservoir, half the cannula, half the oxygen diffusor, etc.).

In operation 2112, a strip of partially cured silicone is added to either an adjoining edge of a partially cured silicone half or to between such edges (thereby extending between the edges) depending on the type of the half. If the half is an interfacing membrane between the chamber and the reservoir, the strip extends between its edges. Otherwise, the strip is local to one of the edges. In operation 2112, the pairs of corresponding halves are also aligned and adjoined along their edges after the addition of the corresponding strips.

In operation 2114, the partially cured silicone halves, as aligned and adjoined, are further cured to create an integrally formed silicone workpiece. The curing is performed at 100° C. for three hours. The workpiece includes the chamber, the reservoir, the cannula, and the oxygen diffusor. The reservoir and the chamber are separated by a silicone membrane (e.g., one of the added silicone strips). The cannula connects the chamber to the oxygen diffusor. These parts are made of silicone and none of them is coated with parylene C at this point in the process. An extraction process can be applied to the cured silicone workpiece to remove any uncured elements. In an example, the extraction process includes soaking the cured silicone workpiece in an organic solvent, such as acetone, heptane, and/or hexane, over a period of time, such as a couple of days.

In operation 2116, a set of electrodes and a metal tube are inserted in the reservoir and the cannula, respectively. The electrodes are made of a biocompatible conductor such as gold or platinum. The metal tube is made of a biocompatible metal, such as steel.

In operation 2118, a coating of parylene C is deposited on the exterior surfaces of the chamber, the reservoir, and the cannula.

In operation 2120, the parylene C and the silicone are removed from an end of the cannula to create a free end. The free end should be connected to the diffusor.

In operation 2122, the free end is inserted and glued to the diffusor, thereby connecting the cannula to the diffusor.

In operation 2124, the silicone workpiece is further cured to strengthen the attachment of the cannula to the diffusor.

In operation 2126, electrolyte is inserted in the reservoir. This can occur after the silicone workpiece is cured.

Figure 22:
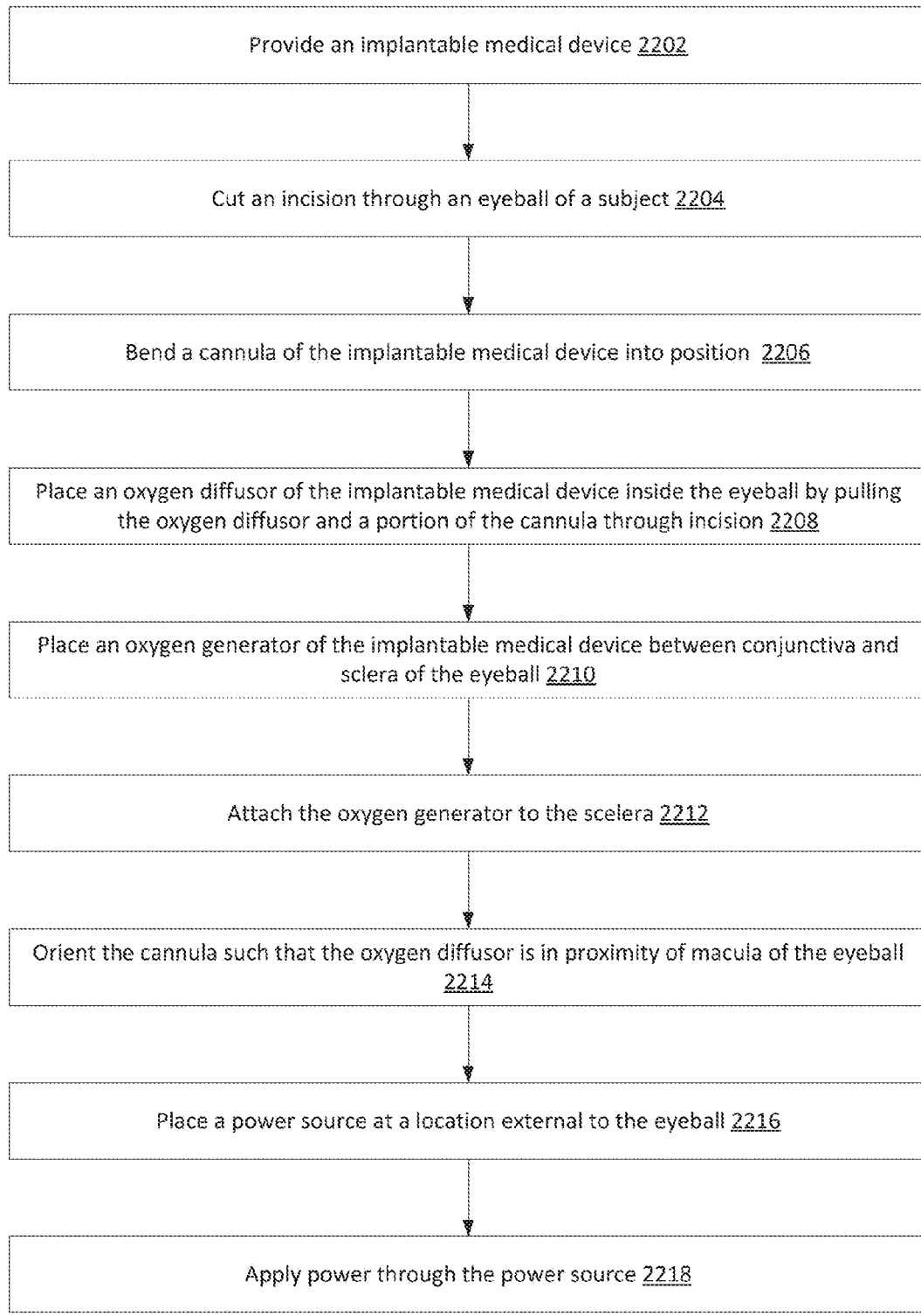
FIG. 22 is a flowchart illustrating a process for using an implantable medical device.

FIG. 22 is a flowchart illustrating a process 2200 for using an implantable medical device. The process 2200 includes inserting the implantable medical device in an eyeball of a subject. This insertion can be performed via a surgical operation. Thereafter, the process 2200 also include causing electrolysis to occur within the implantable medical device based on wireless power. Similar uses are possible in connection with implantations in other parts of a body of the subject.

In operation 2202, the implantable medical device is provided. The implantable medical device includes an oxygen generator, an oxygen diffusor, and a cannula. The oxygen generator is impermeable to oxygen and includes electrolyte reservoir containing electrolyte and a set of electrodes. The oxygen diffusor is permeable to the oxygen. The cannula connects the oxygen generator to the oxygen diffusor.

In operation 2204, an incision is cut through the eyeball. The size of the incision depends on the size of the cannula and the oxygen diffusor. The oxygen diffusor can be foldable, rollable, and/or stretchable, thereby reducing the needed size of the incision. The shape of the oxygen diffusor can also reduce the needed size. In the case of a hook-like shape, the incision need not be larger than the diameter of the interior of the oxygen diffusor. A surgeon can position the oxy diffusor by pushing the hook from the free end through the incision until fully inserted.

In operation 2206, the cannula is bent. For example, the cannula includes a metal plate or strip to facilitate the bending and the holding in position.

In operation 2208, the oxygen diffusor is placed next to targeted tissue, such as the macular. For example, the oxygen diffusor and a portion of the cannula are pulled inside the eyeball through the incision.

In operation 2210, the oxygen generator is placed between the conjunctiva and sclera of the eye.

In operation 2212, the oxygen generator is attached to the sclera. For example, suturing or tacking can be used for this attachment.

In operation 2214, the cannula is oriented that the oxygen diffusor is in proximity of the macula.

In operation 2216, a power source is placed at a location external to the eyeball. For example, an inductive coil of the power source is placed within two centimeters and within a twenty degree angle from the conjunctiva (or, more specifically, from an inductive coil of the oxygen generator). Inductive coupling is used to wireless provided power from the power source to the oxygen generator.

In operation 2218, power is applied through the power source. Inductive coupling occurs. DC voltage is then applied to the set of electrodes of the oxygen generator. The set of electrodes are in contact with the electrolyte in the electrolyte reservoir. The voltage application causes electrolysis, thereby generating oxygen from the electrolyte. The generated oxygen is provided from the electrolyte reservoir via a membrane permeable to oxygen. The generated oxygen is transported via the cannula to the oxygen diffusor for release into the eyeball, by the macula.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" includes within a tolerance of ±0.01%, ±0.1%, ±1%, ±2%, ±3%, ±4%, ±5%, ±8%, ±10%, ±15%, ±20%, ±25%, or as otherwise known in the art. "Substantially" refers to more than 66%, 75%, 80%, 90%, 95%, or, depending on the context within which the term substantially appears, value otherwise as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An implantable medical device comprising:
   a small molecule generator comprising an electrolyte reservoir and a set of electrodes, wherein:
      a portion of the electrolyte reservoir is impermeable to a predetermined class of small molecules, and
      the set of electrodes is disposed inside the electrolyte reservoir and is configured to facilitate electrolysis of the small molecules based on an electric power application to the set of electrodes and on presence of electrolyte inside the electrolyte reservoir;
   a small molecule diffusor, wherein at least a portion of the small molecule diffusor is permeable to the small molecules; and
   a cannula impermeable to the small molecules and comprising a lumen, wherein the lumen connects the small molecule generator to the small molecule diffusor.

2. The implantable medical device of claim 1, further comprising a chamber, wherein at least the chamber and the electrolyte reservoir form a bag that is impermeable to the small molecules, and wherein an end of the cannula is connected to an opening of the bag.

3. The implantable medical device of claim 1, wherein the small molecule diffusor forms a permeable sac, and wherein the lumen and an interior of the permeable sac encloses an oxygen transport substance.

4. The implantable medical device of claim 1, further comprising an absorption bag that is permeable to the small molecules, wherein the cannula comprises material that is impermeable to the small molecules and that splits the lumen in at least two channels, and wherein the cannula comprises a valve disposed at an end of the lumen between a first channel and a second channel formed by the material.

5. The implantable medical device of claim 4, wherein the small molecule diffusor comprises two permeable sacs that share a surface permeable to the small molecules, wherein the first channel is connected to a first permeable sac, and wherein the second channel is connected to a second permeable sac.

6. The implantable medical device of claim 1, further comprising a chamber permeable to the small molecules, wherein the chamber surrounds at least a portion of the electrolyte reservoir, wherein an end of the cannula is connected to an opening of the chamber, and wherein the cannula and the chamber comprise an oxygen transport substance.

7. The implantable medical device of claim 1, wherein the electrodes are arranged in spiral arrangement.

8. The implantable medical device of claim 1, wherein the electrodes are arranged in interleaved arrangement.

9. The implantable medical device of claim 1, wherein the electrodes are distributed along plates.

10. The implantable medical device of claim 1, wherein the electric power application comprises an application of voltage that varies between two and three volts.

11. The implantable medical device of claim 1, further comprising a coil configured to inductively couple circuitry of the implantable medical device to an external power source, wherein the circuitry comprises a microcontroller and is printed on a biocompatible polymer-based substrate.

12. The implantable medical device of claim 11, wherein the electric power application is controlled based on a feedback loop to the microcontroller about the electrolysis of the small molecules, and wherein the feedback loop comprises at least one of a pressure sensor or an oxygen sensor.

13. The implantable medical device of claim 11, wherein the microcontroller is configured to measure an amount of generated small molecules through the electrolysis, and wherein the circuitry further comprises memory configured to store data about the amount of generated small molecules, and a transmitter configured to transmit the data to an external computing device.

14. The implantable medical device of claim 1, further comprising a second electrolyte reservoir and a second cannula that connects the second electrolyte reservoir to the electrolyte reservoir, wherein the electrolyte reservoir is refillable with amounts of the electrolyte, wherein the amounts of electrolyte are available for transport from the second electrolyte reservoir based on a pressure differential between the second electrolyte reservoir and the electrolyte reservoir.

15. The implantable medical device of claim 1, wherein the cannula comprises a small molecule transport substance disposed in the lumen.

16. The implantable medical device of claim 15, wherein the small molecules comprise oxygen molecules, wherein the small molecule transport substance comprises an oxygen transport substance.

17. The implantable medical device of claim 15, further comprising a chamber, wherein at least the chamber and the electrolyte reservoir form a bag that is impermeable to the small molecules, and wherein the chamber comprises another portion of the small molecule transport substance.

18. The implantable medical device of claim 1, wherein a second portion of the electrolyte reservoir is permeable to the small molecules.

19. The implantable medical device of claim 18, further comprising a chamber, wherein at least the chamber and the electrolyte reservoir form a bag that is impermeable to the small molecules, wherein the second portion of the electrolyte reservoir is shared with the chamber, and wherein an end of the cannula is connected to an opening of the chamber.

20. The implantable medical device of claim 19, wherein the small molecule generator is remote from the small molecule diffusor, wherein the cannula is narrower than the bag and the small molecule diffusor, wherein the small molecules comprise oxygen molecules, and wherein the chamber comprises an oxygen transport substance.

* * * * *